(12) United States Patent
Kim et al.

(10) Patent No.: US 7,935,713 B2
(45) Date of Patent: May 3, 2011

(54) GLUCAGON RECEPTOR ANTAGONIST COMPOUNDS, COMPOSITIONS CONTAINING SUCH COMPOUNDS AND METHODS OF USE

(75) Inventors: Ronald M. Kim, Summit, NJ (US); Emma R. Parmee, Scotch Plains, NJ (US); Qiang Tan, Westfield, NJ (US); Cangming Yang, Highland Park, NJ (US); Ashley Rouse Lins, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 296 days.

(21) Appl. No.: 12/227,030

(22) PCT Filed: May 11, 2007

(86) PCT No.: PCT/US2007/011390
§ 371 (c)(1), (2), (4) Date: Nov. 5, 2008

(87) PCT Pub. No.: WO2007/136577
PCT Pub. Date: Nov. 29, 2007

(65) Prior Publication Data
US 2009/0105310 A1    Apr. 23, 2009

Related U.S. Application Data

(60) Provisional application No. 60/800,641, filed on May 16, 2006.

(51) Int. Cl.
*A61K 31/47* (2006.01)
*A61K 31/4184* (2006.01)
*C07D 215/00* (2006.01)
*C07D 235/04* (2006.01)

(52) U.S. Cl. ........ 514/311; 546/112; 546/152; 546/175; 548/301.7; 548/304.4; 548/309.7; 548/217; 514/299; 514/385; 514/394

(58) Field of Classification Search .................. 546/112, 546/152, 174, 175; 548/301.7, 304.4, 309.7, 548/215, 217; 514/299, 311, 385, 394
See application file for complete search history.

(56) References Cited

U.S. PATENT DOCUMENTS

| | | | |
|---|---|---|---|
| 5,776,954 A | 7/1998 | deLaszlo et al. | |
| 5,965,741 A | 10/1999 | Breault et al. | |
| 6,765,009 B2 | 7/2004 | Francesco et al. | |
| 7,151,114 B2 | 12/2006 | Stelmach et al. | |
| 7,687,534 B2 * | 3/2010 | Stelmach et al. | 514/415 |
| 7,803,951 B2 * | 9/2010 | Liang et al. | 548/251 |
| 2004/0209928 A1 | 10/2004 | Kurukulasuriya et al. | |
| 2005/0256175 A1 | 11/2005 | Lau et al. | |
| 2008/0161347 A1 | 7/2008 | Stelmach et al. | |

FOREIGN PATENT DOCUMENTS

| | | |
|---|---|---|
| CA | 2 569 459 A1 | 12/2005 |
| EP | 1 489 077 | 12/2004 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 99/01423 | 1/1999 |
| WO | WO 99/32448 | 7/1999 |
| WO | WO 00/39088 | 7/2000 |
| WO | WO 00/69810 | 11/2000 |
| WO | WO 02/00612 | 1/2002 |
| WO | WO 02/40444 | 5/2002 |
| WO | WO 03/048109 | 6/2003 |
| WO | WO 03/051357 | 6/2003 |
| WO | WO 03/053938 | 7/2003 |
| WO | WO 03/064404 | 8/2003 |
| WO | WO 03/097619 | 11/2003 |
| WO | WO 2004/002480 | 1/2004 |
| WO | WO 2004/050039 | 6/2004 |
| WO | WO 2004/056763 | 7/2004 |
| WO | WO 2004/062663 | 7/2004 |
| WO | WO 2004/069158 | 8/2004 |
| WO | WO 2005/058845 | 6/2005 |

* cited by examiner

*Primary Examiner* — Golam M Shameem
(74) *Attorney, Agent, or Firm* — Heidi M. Struse; Richard C. Billups

(57) ABSTRACT

Glucagon receptor antagonist compounds are disclosed. The compounds are useful for treating type 2 diabetes and related conditions. Pharmaceutical compositions and methods of treatment are also included.

14 Claims, No Drawings

… (1)

GLUCAGON RECEPTOR ANTAGONIST COMPOUNDS, COMPOSITIONS CONTAINING SUCH COMPOUNDS AND METHODS OF USE

CROSS-REFERENCE TO RELATED APPLICATIONS

This application is a U.S. National Phase application under 35 U.S.C. §371 of PCT Application No. PCT/US2007/011390, filed May 11, 2007, which published as WO 2007/136577 on Nov. 29, 2007, and claims priority under 35 U.S.C. §119 from U.S. Provisional Application No. 60/800,641, filed May 16, 2006.

BACKGROUND OF THE INVENTION

The present invention relates to glucagon receptor antagonist compounds, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level>126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure>130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of the glucagon receptor are useful in improving insulin responsiveness in the liver, decreasing the rate of gluconeogenesis and glycogenolysis, and lowering the rate of hepatic glucose output resulting in a decrease in the levels of plasma glucose.

SUMMARY OF THE INVENTION

A compound represented by formula I:

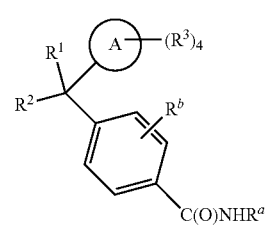

or a pharmaceutically acceptable salt or solvate thereof, wherein:

Ring A represents a bicyclic Aryl or 8-10 membered bicyclic heteroaryl group containing 1-3 heteroatoms, 0-1 of which are O or S, and 0-2 of which are N atoms;

$R^1$ is selected from $C_{1-10}$alkyl and $C_{2-10}$alkenyl, said groups being optionally substituted with: 1-5 halo groups, up to perhalo, and 1 member selected from OH, $CO_2R^4$, $SO_pR^5$, CN, $NO_2C(O)NR^6R^7$, $NR^6R^7$, $OC_{1-6}$alkyl, $C_{1-6}$haloalkoxy, halo$C_{1-6}$alkylthio, Aryl and Heteroaryl, said Aryl and Heteroaryl being optionally substituted with 1-3 halo groups and 1-2 members selected from the group consisting of: OH, $CO_2R^4$, $SO_pR^5$, CN, $NO_2$, $C(O)NR^6R^7$, $NR^6R^7$; $C_{1-6}$alkyl, halo$C_{1-6}$alkyl, $C(O)C_{1-6}$alkyl, C(O)-halo$C_{1-6}$alkyl, $OC_{1-6}$alkyl, halo$C_{1-6}$alkoxy $C_{2-6}$alkenyl, halo$C_{2-6}$alkenyl, $SC_{1-6}$alkyl and halo$SC_{1-6}$alkyl;

$R^2$ represents hydrogen, $C_{1-6}$alkyl or halo$C_{1-6}$alkyl;

four $R^3$ groups are present as follows:

1) 0-1 $R^3$ group is selected from the group consisting of: Aryl, HAR, —$C_{1-4}$Alkyl-Aryl, —$C_{1-4}$Alkyl-HAR, —X-Aryl, —X-HAR, —X—$C_{1-4}$Alkyl-Aryl and —X—$C_{1-4}$Alkyl-HAR; wherein X represents O, S, S(O) or $S(O)_2$;

said Aryl and HAR groups and portions of the groups above being optionally substituted with 1-4 halo atoms, and 1-2 members selected from: OH, CN, $C_{1-6}$alkyl, $OC_{1-6}$alkyl, halo$C_{1-6}$alkyl, $OC_{1-6}$haloalkyl, $NO_2$, $SO_pR^5$, $C_{2-6}$alkenyl, $OC_{2-6}$alkenyl and $NR^6R^7$;

2) 0-3 $R^3$ groups are selected from: OH, CN, oxo, $NO_2$, $SO_pR^5$, $NR^6R^7$, $C_{1-8}$alkyl, halo$C_{1-8}$alkyl, $OC_{1-8}$alkyl, $OC_{1-8}$haloalkyl, $C_{2-8}$alkenyl, $OC_{2-8}$alkenyl and halo$C_{2-8}$alkenyl, and 3) any remaining $R^3$ groups are H or halo atoms;

$R^4$ is H or $C_{1-6}$alkyl, and $R^5$ represents a member selected from the group consisting of: $C_{1-8}$alkyl, halo$C_{1-6}$alkyl, Aryl or Ar—$C_{1-4}$alkyl;

$R^6$ and $R^7$ each independently represent H or $C_{1-6}$alkyl;

p is 0, 1 or 2;

$R^a$ represents $CH_2CH_2CO_2R^4$, $CH_2CH(OH)CO_2R^4$ or 5-tetrazolyl; and $R^b$ is H or is selected from the group consisting of: halo, CN, $NO_2$, OH, $C_{1-3}$alkyl, $OC_{1-3}$alkyl, halo$C_{1-3}$alkyl and halo$C_{1-3}$alkoxy.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine.

One aspect of the invention relates to a compound represented by formula I:

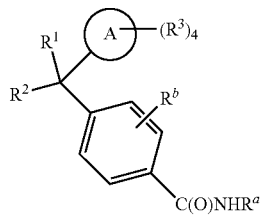

I or a pharmaceutically acceptable salt or solvate thereof, wherein:

Ring A represents a bicyclic Aryl or 8-10 membered bicyclic heteroaryl group containing 1-3 heteroatoms, 0-1 of which are O or S, and 0-2 of which are N atoms;

$R^1$ is selected from $C_{1-10}$alkyl and $C_{2-10}$alkenyl, said groups being optionally substituted with: 1-5 halo groups, up to perhalo, and 1 member selected from OH, $CO_2R^4$, $SO_pR^5$, CN, $NO_2C(O)NR^6R^7$, $NR^6R^7$, $OC_{1-6}$alkyl, $C_{1-6}$haloalkoxy, halo$C_{1-6}$alkylthio, Aryl and Heteroaryl, said Aryl and Heteroaryl being optionally substituted with 1-3 halo groups and 1-2 members selected from the group consisting of: OH, $CO_2R^4$, $SO_pR^5$, CN, $NO_2$, $C(O)NR^6R^7$, $NR^6R^7$; $C_{1-6}$alkyl, halo$C_{1-6}$alkyl, $C(O)C_{1-6}$alkyl, $C(O)$-halo$C_{1-6}$alkyl, $OC_{1-6}$alkyl, halo$C_{1-6}$alkoxy $C_{2-6}$alkenyl, halo$C_{2-6}$alkenyl, $SC_{1-6}$alkyl and haloS$C_{1-6}$alkyl;

$R^2$ represents hydrogen, $C_{1-6}$alkyl or halo$C_{1-6}$alkyl;

four $R^3$ groups are present as follows:
1) 0-1 $R^3$ group is selected from the group consisting of: Aryl, HAR, —$C_{1-4}$Alkyl-Aryl, —$C_{1-4}$Alkyl-HAR, —X-Aryl, —X-HAR, —X—$C_{1-4}$Alkyl-Aryl and —X—$C_{1-4}$Alkyl-HAR; wherein X represents O, S, S(O) or $S(O)_2$;

said Aryl and HAR groups and portions of the groups above being optionally substituted with 14 halo atoms, and 1-2 members selected from: OH, CN, $C_{1-6}$alkyl, $OC_{1-6}$alkyl, halo$C_{1-6}$alkyl, $OC_{1-6}$haloalkyl, $NO_2$, $SO_pR^5$, $C_{2-6}$alkenyl, $OC_{2-6}$alkenyl and $NR^6R^7$;

2) 0-3 $R^3$ groups are selected from: OH, CN, oxo, $NO_2$, $SO_pR^5$, $NR^6R^7$, $C_{1-8}$alkyl, halo$C_{1-8}$alkyl, $OC_{1-8}$alkyl, $OC_{1-8}$haloalkyl, $C_{2-8}$alkenyl, $OC_{2-8}$alkenyl and halo$C_{2-8}$alkenyl, and 3) any remaining $R^3$ groups are H or halo atoms;

$R^4$ is H or $C_{1-6}$alkyl, and $R^5$ represents a member selected from the group consisting of: $C_{1-8}$alkyl, halo$C_{1-6}$alkyl, Aryl or Ar—$C_{1-4}$alkyl;

$R^6$ and $R^7$ each independently represent H or $C_{1-6}$alkyl;

p is 0, 1 or 2;

$R^a$ represents $CH_2CH_2CO_2R^4$, $CH_2CH(OH)CO_2R^4$ or 5-tetrazolyl; and $R^b$ is H or is selected from the group consisting of: halo, CN, $NO_2$, OH, $C_{1-3}$alkyl, $OC_{1-3}$alkyl, halo$C_{1-3}$alkyl and halo$C_{1-3}$alkoxy.

An aspect of the invention that is of interest relates to compounds of formula I or a pharmaceutically acceptable salt or solvate thereof wherein ring A is selected from the group consisting of naphthyl and bicyclic 9-10 membered heteroaryl containing 1-3 heteroatoms, 0-1 of which is an oxygen or sulfur atom and 0-2 of which are nitrogen atoms. Within this subset of the invention, all other variables are as originally defined.

More particularly, an aspect of the invention that is of interest relates to compounds of formula I or a pharmaceutically acceptable salt or solvate thereof wherein ring A is selected from the group consisting of naphthyl, quinolinyl, benzimidazolyl, benzothiazolyl, benzofuranyl and benzoxazolyl. Within this subset of the invention, all other variables are as originally defined.

Another aspect of the invention that is of interest relates to compounds of formula I or a pharmaceutically acceptable salt or solvate thereof wherein $R^1$ represents a $C_{1-8}$alkyl group or a $C_{2-8}$alkenyl group, said groups being optionally substituted with 1-3 halo atoms, and further optionally substituted with 1 group selected from: OH, $SO_pR^5$, $OC_{1-3}$alkyl, $haloC_{1-3}$alkoxy, Aryl and HAR, said Aryl and HAR being optionally substituted with 1-3 halo atoms, and 1-2 groups selected from $SO_pR^5$, $C_{1-6}$alkyl, $haloC_{1-6}$alkyl, $OC_{1-6}$alkyl and $haloC_{1-6}$alkoxy. Within this subset of the invention, all other variables are as originally defined.

More particularly, another aspect of the invention that is of interest relates to compounds of formula I or a pharmaceutically acceptable salt or solvate thereof wherein $R^1$ represents a $C_{1-8}$alkyl or a $C_{2-8}$alkenyl group, said groups being optionally substituted with 1-3 halo atoms, and further optionally substituted with 1 group selected from $SO_pR^5$ Aryl and HAR, wherein p represents 0, $R^5$ represents $C_{1-4}$alkyl, and said Aryl and HAR being optionally substituted with 1-3 halo atoms, and 1 group selected from $SO_pR^5$, $C_{1-6}$alkyl, $haloC_{1-6}$alkyl, $OC_{1-6}$alkyl and $haloC_{1-6}$alkoxy. Within this subset of the invention, all other variables are as originally defined.

Another aspect of the invention that is of interest relates to compounds of formula I or a pharmaceutically acceptable salt or solvate thereof wherein $R^2$ is selected from the group consisting of: H, $C_{1-4}$alkyl and $haloC_{1-4}$alkyl. Within this subset of the invention, all other variables are as originally defined.

Another aspect of the invention that is of interest relates to compounds of formula I or a pharmaceutically acceptable salt or solvate thereof wherein:

four $R^3$ groups are present as follows:
1) 0-1 $R^3$ group is selected from the group consisting of: Aryl, HAR, —$C_{1-4}$Alkyl-Aryl, —X—$(CH_2)_{1-4}$Aryl, —$C_{1-4}$Alkyl-HAR and —X—$(CH_2)_{1-4}$-HAR
wherein X represents O or S and said Aryl and HAR groups and portions of the groups above being optionally substituted with 1-3 halo atoms, and 1-2 members selected from: $C_{1-6}$alkyl, $OC_{1-6}$alkyl, $haloC_{1-6}$alkyl, $OC_{1-6}$haloalkyl, $SO_pR^5$, $C_{2-6}$alkenyl, $OC_{2-6}$alkenyl, and CN;
2) 0-3 $R^3$ groups selected from: CN, $NO_2$, $SO_pR^5$, $C_{1-8}$alkyl, $haloC_{1-8}$alkyl, $OC_{1-8}$alkyl, $OC_{1-8}$haloalkyl and $C_{2-8}$alkenyl, and
3) any remaining $R^3$ groups are H or halo atoms. Within this subset of the invention, all other variables are as originally defined.

In particular, another aspect of the invention that is of interest relates to compounds of formula I or a pharmaceutically acceptable salt or solvate thereof wherein:

four $R^3$ groups are present as follows:
1) 0-1 $R^3$ group is selected from the group consisting of: Phenyl, 5-6 membered HAR, —$(CH_2)_{1-2}$Phenyl, —X—$(CH_2)_{1-2}$Phenyl, —$(CH_2)_{1-2}$-5-6 membered HAR and —X—$(CH_2)_{1-2}$-5-6 membered HAR
wherein X represents O or S and said Aryl and HAR groups and portions of the groups above are optionally substituted with 1-3 halo atoms, and 1 member selected from: $C_{1-6}$allyl, $OC_{1-6}$alkyl, $haloC_{1-6}$alkyl, $OC_{1-6}$haloalkyl, $SO_pR^5$, $C_{2-6}$alkenyl, $OC_{2-6}$alkenyl and CN;
2) 0-3 $R^3$ groups are selected from: CN, $NO_2$, $SO_pR^5$, $C_{1-8}$alkyl, $haloC_{1-8}$alkyl, $OC_{1-8}$alkyl, $OC_{1-8}$haloalkyl and $C_{2-8}$alkenyl, wherein p represents 0 and $R^5$ represents $C_{1-6}$alkyl or $haloC_{1-6}$alkyl,
and
3) any remaining $R^3$ groups are H or halo atoms selected from Cl and F. Within this subset of the invention, all other variables are as originally defined.

Another aspect of the invention that is of interest relates to compounds of formula I or a pharmaceutically acceptable salt or solvate thereof wherein $R^a$ is selected from

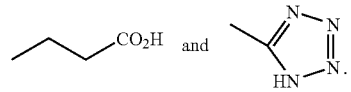

Within this subset of the invention, all other variables are as originally defined with respect to formula I More particularly, an aspect of the invention that is of interest relates to a compound of formula I or a pharmaceutically acceptable salt or solvate thereof wherein $R^a$ represents

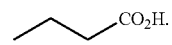

Within this subset of the invention, all other variables are as originally defined with respect to formula I.

Another aspect of the invention that is of interest relates to a compound of formula I or a pharmaceutically acceptable salt or solvate thereof wherein $R^b$ represents H. Within this subset of the invention, all other variables are as originally defined with respect to formula I.

More particularly, an aspect of the invention that is of interest relates to a compound of formula I or a pharmaceutically acceptable salt or solvate thereof, wherein:

ring A is selected from the group consisting of naphthyl and bicyclic 9-10 membered heteroaryl containing 1-3 heteroatoms, 0-1 of which is an oxygen or sulfur atom and 0-2 of which are nitrogen atoms;

$R^1$ represents a $C_{1-8}$alkyl group or a $C_{2-8}$alkenyl group, said groups being optionally substituted with 1-3 halo atoms, and further optionally substituted with 1 group selected from: OH, $SO_pR^5$, $OC_{1-3}$alkyl, $haloC_{1-3}$alkoxy, Aryl and HAR, said Aryl and HAR being optionally substituted with 1-3 halo atoms, and 1-2 groups selected from $SO_pR^5$, $C_{1-6}$alkyl, $haloC_{1-6}$alkyl, $OC_{1-6}$alkyl and $haloC_{1-4}$alkoxy;

$R^2$ is selected from the group consisting of: H, $C_{1-4}$alkyl and $haloC_{1-4}$alkyl;

four $R^3$ groups are present as follows:
1) 0-1 $R^3$ group is selected from the group consisting of: Aryl, HAR, —$C_{1-4}$Alkyl-Aryl, —X—$(CH_2)_{1-4}$Aryl, —$C_{1-4}$Alkyl-HAR and —X—$(CH_2)_{1-4}$-HAR;
wherein X represents O or S and said Aryl and HAR groups and portions of the groups above being optionally substituted with 1-3 halo atoms, and 1-2 members selected from: $C_{1-6}$alkyl, $OC_{1-6}$alkyl, $haloC_{1-6}$alkyl, $OC_{1-6}$haloalkyl, $SO_pR^5$, $C_{2-6}$alkenyl, $OC_{2-6}$alkenyl, and CN;
2) 0-3 $R^3$ groups selected from: CN, $NO_2$, $SO_pR^5$, $C_{1-8}$alkyl, $haloC_{1-8}$alkyl, $OC_{1-8}$alkyl, $OC_{1-8}$haloalkyl and $C_{2-6}$alkenyl, and
3) any remaining $R^3$ groups are H or halo atoms;

$R^a$ is selected from:

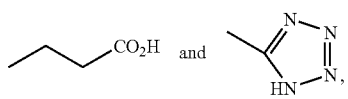

and $R^b$ represents H. Within this subset of the invention, all other variables are as originally defined with respect to formula I.

Examples of compounds that fall within the invention described herein are in the tables contained herein. Pharmaceutically acceptable salts and solvates of the compounds disclosed in the tables are included as well.

Another aspect of the invention that is of interest relates to a pharmaceutical composition comprising a compound as described above with respect to formula I in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I in an amount that is effective to treat type 2 diabetes mellitus.

Another aspect of the invention that is of interest relates to a method of delaying the onset of type 2 diabetes mellitus in a mammalian patient in need thereof, comprising administering to the patient a compound as described above in accordance with formula I in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I as described above.

Another aspect of the invention that is of interest relates to a method of treating obesity in a mammalian patient in need of such treatment comprising administering to said patient a compound in accordance with formula I as described above in an amount that is effective to treat obesity.

Another aspect of the invention that is of interest relates to a method of treating Syndrome X in a mammalian patient in need of such treatment, comprising administering to said patient a compound in accordance with formula I as described above in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I in an amount that is effective to treat said lipid disorder.

Another aspect of the invention that is of interest relates to a method of treating atherosclerosis in a mammalian patient in need of such treatment, comprising administering to said patient a compound in accordance with formula I as described above in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above in an amount that is effective to treat said condition.

Another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above in an amount that is effective to delay the onset of said condition.

Another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, and a compound selected from the group consisting of:

(a) DPP-IV inhibitors, such as sitagliptin, vildagliptin and saxagliptin, as well as the compounds disclosed in U.S. Pat. No. 6,699,871B1 granted on Mar. 2, 2004; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants (ix) LXR modulators, and (x) CETP inhibitors, such as torcetrapib; (k) PPAR delta agonists; (l) antiobesity compounds; (m) an ileal bile acid transporter inhibitor; (n) anti-inflammatory agents excluding glucocorticoids; (o) protein tyrosine phosphatase-1B (PTP-IB) inhibitors, and (p) CB1 antagonists/inverse agonists, such as rimonabant and those disclosed in WO03/077847A2, published on Sep. 25, 2003, and WO05/000809 published on Jan. 6, 2005, incorporated herein by reference, said compounds being administered to the patient in amounts that are effective to treat said condition.

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of lovastatin, simvastatin, pravastatin, fluvastatin, atorvastatin, itavastatin, ZD-4522 and rivastatin.

Another aspect of the invention that is of interest relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment therapeutically effective amounts of a compound of formula I as described above and an HMG-CoA reductase inhibitor.

Another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin.

Even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin selected from the group consisting of: lovastatin, simvastatin, pravastatin, fluvastatin, atorvastatin, itavastatin, ZD-4522 and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin.

Another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a pharmaceutical composition comprising (1) a compound of formula I as described above; (2) a compound selected from the group consisting of: (a) DPP-IV inhibitors, such as sitagliptin, vildagliptin, saxagliptin, as well as those disclosed in U.S. Pat. No. 6,699,871B1 granted on Mar. 2, 2004; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics and GLP-1 receptor agonists; (h) GIP, GIP mimetics and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA: cholesterol acyltransferase inhibitors, (viii) anti-oxidants, (ix) LXR modulators and (x) CETP inhibitors, such as torcetrapib; (k) PPAR delta agonists; (l) antiobesity compounds; (m) an ileal bile acid transporter inhibitor; (n) anti-inflammatory agents other than glucocorticoids; (o) protein tyrosine phosphatase-1B (PTP-1B) inhibitors; and (p) CB1 antagonist/inverse agonists, such as rimonabant, and those disclosed in WO03/077847A2 published on Sep. 25, 2003 and WO05/000809 published on Jan. 6, 2005, and (3) a pharmaceutically acceptable carrier.

One pharmaceutical composition that is of interest is comprised of a compound of formula I as described herein, or a pharmaceutically acceptable salt or solvate thereof, in combination with a DPP-IV inhibitor selected from the group consisting of:

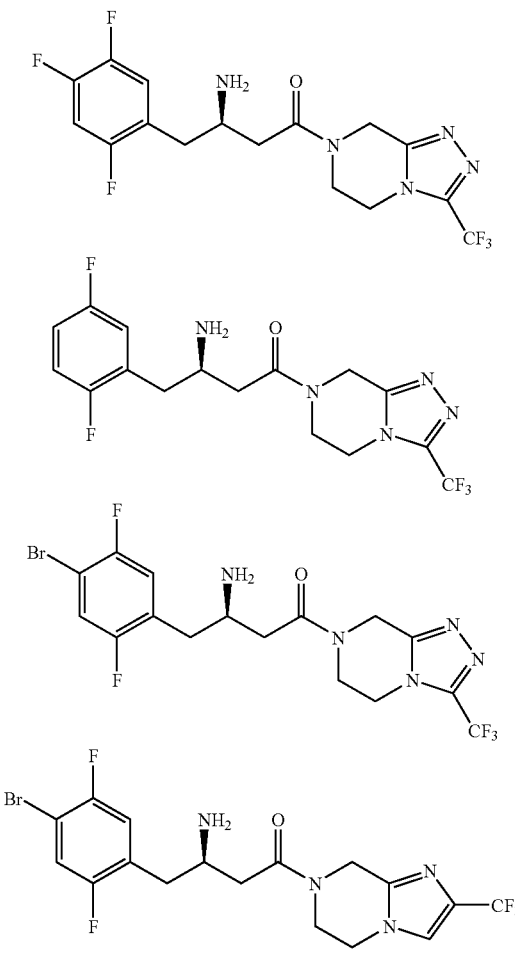

or a pharmaceutically acceptable salt or solvate thereof in combination with a pharmaceutically acceptable carrier.

Another pharmaceutical composition that is of particular interest is comprised of a compound of formula I as described herein, or a pharmaceutically acceptable salt or solvate thereof, in combination with a CB1 receptor antagonist/inverse agonist, in combination with a pharmaceutically acceptable carrier. Examples of CB1 antagonist/inverse agonists that are of particular interest in the invention described herein include rimonabant, the following which are disclosed in WO03/077847A2 published on Sep. 25, 2003:

(1) N-[3-(4-chlorophenyl)-1-methyl-2-phenylpropyl]-2-(4-chlorophenyloxy)-2-methylpropanamide;
(2) N-[3-(4-chlorophenyl)-1-methyl-2-phenylpropyl]-2-(2-pyridyloxy)-2-methylpropanamide;
(3) N-[3-(4-chlorophenyl)-1-methyl-2-(3-pyridyl)propyl]-2-(4-chlorophenyloxy)-2-methylpropanamide;
(4) N-[3-(4-chlorophenyl)-1-methyl-2-phenylpropyl]-2-(3,5-difluorophenyloxy)-2-methylpropanamide;
(5) N-[3-(4-chlorophenyl)-2-phenyl-1-methylpropyl]-2-(3,5-dichlorophenyloxy)-2-methylpropanamide;
(6) N-[3-(4-chlorophenyl)-1-methyl-2-phenylpropyl]-2-(3-chlorophenyloxy)-2-methylpropanamide;
(7) N-[3-(4-chlorophenyl)-2-(3,5-difluorophenyl)-1-methylpropyl]-2-(2-pyridyloxy)-2-methylpropanamide;
(8) N-[3-(4-chlorophenyl)-1-methyl-2-phenyl-propyl]-2-(5-chloro-2-pyridyloxy)-2-methylpropanamide;
(9) N-[3-(4-chlorophenyl)-1-methyl-2-phenylpropyl]-2-(6-methyl-pyridyloxy)-2-methylpropanamide;
(10) N-[3-(4-chlorophenyl)-1-methyl-2-phenylpropyl]-2-(phenyloxy)-2-methylpropanamide;
(11) N-[(3-(4-chlorophenyl)-1-methyl-2-phenylpropyl]-2-(5-trifluoromethylpyridyloxy)-2-methylpropanamide;
(12) N-[3-(4-chlorophenyl)-2-(3-pyridyl)-1-methylpropyl]-2-(5-trifluoromethyl-2-pyridyloxy)-2-methylpropanamide;
(13) N-[3-(4-chlorophenyl)-2-(3-cyanophenyl)-1-methylpropyl]-2-(5-trifluoromethyl-2-pyridyloxy)-2-methylpropanamide;
(14) N-[3-(4-chlorophenyl)-2-(5-chloro-3-pyridyl)-1-methylpropyl]-2-(5-trifluoromethyl-2-pyridyloxy)-2-methylpropanamide;
(15) N-[3-(4-chlorophenyl)-2-(5-methyl-3-pyridyl)-1-methylpropyl]-2-(5-trifluoromethyl-2-pyridyloxy)-2-methylpropanamide;
(16) N-[3-(4-chlorophenyl)-2-(5-cyano-3-pyridyl)-1-methylpropyl]-2-(5-trifluoromethyl-2-pyridyloxy)-2-methylpropanamide;
(17) N-[3-(4-chlorophenyl)-2-(3-methylphenyl)-1-methylpropyl]-2-(5-trifluoromethyl-2-pyridyloxy)-2-methylpropanamide;
(18) N-[3-(4-chlorophenyl)-2-phenyl-1-methylpropyl]-2-(4-trifluoromethyl-2-pyridyloxy)-2-methylpropanamide;
(19) N-[3-(4-chlorophenyl)-2-phenyl-1-methylpropyl]-2-(4-trifluoromethyl-2-pyrimidyloxy)-2-methylpropanamide;
(20) N-[3-(4-chlorophenyl)-1-methyl-2-(thiophen-3-yl)propyl]-2-(5-chloro-2-pyridyloxy)-2-methylpropanamide;
(21) N-[3-(5-chloro-2-pyridyl)-2-phenyl-1-methylpropyl]-2-(5-trifluoromethyl-2-pyridyloxy)-2-methylpropanamide;
(22) N-[3-(4-methyl-phenyl)-1-methyl-2-phenylpropyl]-2-(4-trifluoromethyl-phenyloxy)-2-methylpropanamide;
(23) N-[3-(4-fluoro-phenyl)-2-(3-cyano-phenyl)-1-methylpropyl]-2-(5-trifluoromethyl-2-pyridyloxy)-2-methylpropanamide;
(24) N-[3-(4-chlorophenyl)-2-(1-indolyl)-1-methyl)propyl]-2-(5-trifluoromethyl-2-oxypyridine-2-yl)-2-methylpropanamide;
(25) N-[3-(4-chlorophenyl)-2-(7-azaindol-N-yl)-1-methyl)propyl]-2-(5-trifluoromethyl-2-pyridyloxy)-2-methylpropanamide;
(26) N-[3-(4-chloro-phenyl)-2-(1-indolinyl)-1-methylpropyl]-2-(5-trifluoromethyl-2-pyridyloxy)-2-methylpropanamide;

(27) N-[3-(4-chloro-phenyl)-2-(N-methyl-anilino)-1-methylpropyl]-2-(5-trifluoromethyl-2-pyridyloxy)-2-methylpropanamide;
(28) N-[3-(4-methoxy-phenyl)-2-(3-cyano-phenyl)-1-methylpropyl]-2-(5-trifluoromethyl-2-pyridyloxy)-2-methylpropanamide;
(29) N-[3-(4-chlorophenyl)-2-(3-cyanophenyl)-1-methylpropyl]-2-(6-trifluoromethyl-4-pyrimidyloxy)-2-methylpropanamide;
(30) N-[2-(3-cyanophenyl)-1,4-dimethylpentyl]-2-(5-trifluoromethyl-2-pyridyloxy)-2-methylpropanamide;
(31) N-[3-(4-chlorophenyl)-2-(1-oxido-5-cyano-3-pyridyl]-1-methylpropyl]-2-(5-trifluoromethyl-2-pyridyloxy)-2-methylpropanamide;
(32) N-[2-(3-cyanophenyl)-3-cyclobutyl-1-methylpropyl]-2-(5-trifluoromethyl-2-pyridyloxy)-2-methylpropanamide;
(33) N-[2-(3-cyanophenyl)-1-methyl-heptyl]-2-(5-trifluoromethyl-2-pyridyloxy)-2-methylpropanamide,
(34) N-[2-(3-cyanophenyl)-3-cyclopentyl-1-methylpropyl]-2-(5-trifluoromethyl-2-pyridyloxy)-2-methylpropanamide;
(35) N-[2-(3-cyanophenyl)-3-cyclohexyl-1-methylpropyl]-2-(5-trifluoromethyl-2-pyridyloxy)-2-methylpropanamide;
and in WO05/000809 published on Jan. 6, 2005, which includes the following:
3-{1-[Bis(4-chlorophenyl)methyl]azetidin-3-ylidene}-3-(3,5-difluorophenyl)-2,2-dimethylpropanenitrile
1-{1-[1-(4-chlorophenyl)pentyl]azetidin-3-yl}-1-(3,5-difluorophenyl)-2-methylpropan-2-ol
3-((S)-(4-chlorophenyl) {3-[(1S)-1-(3,5-difluorophenyl)-2-hydroxy-2-methylpropyl]azetidin 1-yl}methyl)benzonitrile
3-((S)-(4-chlorophenyl) {3-[(1S)-1-(3,5-difluorophenyl)-2-fluoro-2-methylpropyl]azetidin-1-yl}methyl)benzonitrile
3-((4-chlorophenyl) {3-[1-(3,5-difluorophenyl)-2,2-dimethylpropyl]azetidin-1-yl}methyl)benzonitrile
3-((1S)-1-{1-[(S)-(3-cyanophenyl)(4-cyanophenyl)methyl]azetidin-3-yl}-2-fluoro-2-methylpropyl)-5-fluorobenzonitrile
3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile and
5-((4-chlorophenyl){3-[(1S)-1-(3,5-difluorophenyl)-2-fluoro-2-methylpropyl]azetidin-1-yl}methyl)thiophene-3-carbonitrile,
as well as the pharmaceutically acceptable salts and solvates thereof, in combination with a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

This invention relates to a method of inhibiting the activity of glucagon by antagonizing the glucagon receptor, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

When used in combination with other agents, the dosages noted above for the glucagon antagonist are provided along with the usual dose for the other medication. For example, when a DPP-IV inhibitor such as those disclosed in U.S. Pat. No. 6,699,871B1, is included, the DPP-IV inhibitor can be used in an amount ranging from about 1.0 mg to as high as about 1000 mg, preferably about 2-5 mg to about 250 mg, and in particular, about 50 mg or about 100 mg administered in single daily doses or in divided doses as appropriate. Similarly, when the glucagon receptor antagonist is used in combination with a CB1 antagonist/inverse agonist, the CB1 antagonist/inverse agonist can be used in an amount ranging from as low as about 0.1 mg to as high as about 1000 mg, more particularly, in an amount ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg and 10 mg.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of Formula I:

| Injectable Suspension (im.) | mg/mL | Tablet | Mg/tablet |
|---|---|---|---|
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.35 |
| Benzalkonium chloride | 1.0 | Magnesium Stearate | 2.5 |
| Water for injection | t.d. 1.0 mL | Total | 500 mg |
| Capsule | mg/capsule | Aerosol | Per Canister |
| Compound of Formula 1 | 25.0 | Compound of Formula 1 | 250 mg |
| Lactose | 735 | Lecithin, NF Liq. Conc. | 1.2 mg |
| Mg Stearate | 1.5 | Trichloromethane, NF | 4.025 g |
| Total | 600 mg | Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, such as sitagliptin, vildagliptin, saxagliptin, and the like, such as those disclosed in U.S. Pat. No. 6,699,871B1 granted on Mar. 2, 2004 (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide), and CB1 inhibitors, such as rimonabant and those compounds disclosed in WO03/077847A2 published on Sep. 25, 2003 and in WO05/000809 A1 published on Jan. 6, 2005.

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include: (1) a compound according to formula I, (2) a compound selected from the group consisting of: (a) DPP-IV inhibitors such as sitagliptin, vildagliptin, saxagliptin and the like; (b) insulin sensitizers selected from the group consisting of (i) PPAR agonists and (ii) biguanides; (c) insulin and insulin mimetics; (d) sulfonylureas and other insulin secretagogues; (e) α-glucosidase inhibitors; (f) CB1 receptor antagonists/inverse agonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants, (ix) LXR modulators and (x) CETP inhibitors, such as torcetrapib; (k) PPAR delta agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; (p) CB1 antagonist/inverse agonists and (3) a pharmaceutically acceptable carrier.

The compounds of formula I can be synthesized in accordance with the general schemes provided below where $R^1$-$R^3$, $R^a$, $R^b$ and A are defined as above, taking into account the specific examples that are provided. Throughout the synthesis schemes, abbreviations are used with the following meanings unless otherwise indicated:

| | |
|---|---|
| aq = aqueous | BuLi, n-BuLi = n-butyllithium |
| Bu = butyl, t-Bu = t-butyl | Bn and Bnzl = benzyl |
| BOC, Boc = t-butyloxycarbonyl | CBZ, Cbz = Benzyloxycarbonyl |
| COD = cyclooctadiene | DCM = dichloromethane |
| CDI = carbonyl diimidazole | DIAD = diisopropylazodicarboxylate |
| DCC = Dicyclohexylcarbodiimide | DMAP = 4-Dimethylaminopyridine |
| DIEA = diisopropylethylamine | DMF = N,N-dimethylformamide |
| DMAC, DMA = dimethylacetamide | EtOH = ethanol |
| EDC = 1-ethyl-3-(3-dimethylaminopropyl)-carbodiimide | FAB-mass spectrum = Fast atom bombardment-mass pectroscopy |
| dppf = 1,1'-bis(diphenylphosphino) ferrocene | LCMS = liquid chromatography - mass spectroscopy |
| EtOAc = ethyl acetate | HPLC = High pressure liquid chromatography |
| eq. = equivalent(s) | LAH = Lithium aluminum hydride |
| HOAc = acetic acid | ESI = electrospray ionization |
| HOBT, HOBt = Hydroxybenztriazole | MeCN, $CH_3CN$ = acetonitrile |
| LHMDS = lithium bis(trimethylsilyl)amide | Pd/C = palladium on activated carbon |
| MeOH = methanol | TFA = Trifluoroacetic acid |
| Me = methyl | $NMe_2$ = dimethylamino |
| PBS = phosphate buffer saline | triflate = trifluoromethanesulonate |
| Ph = phenyl | IPA = isopropanol |
| THF = tetrahydrofuran | Py, Pyr = pyridyl |
| $C_6H_{11}$ = cyclohexyl | PyBOP = Benzotrazol-1-yloxytripyrrolidinophosphonium hexafluorophosphate |
| iPr = isopropyl | RT, rt = room temperature |
| 2,4-diClPh = 2,4-dichlorophenyl | Xantphos = 4,5-bis(diphenylphosphino)-9,9-dimethylxanthene |

In one embodiment of the present invention, the compounds I may be prepared from alkyl 4-(1-aryl-alkyl)benzoate intermediates 1, where $R^i$=$C_1$-$C_4$ alkyl. Such compounds 1 may be prepared by a variety of procedures by those skilled in the art.

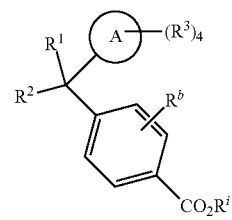

1

One example for preparation of compounds 1 is shown in Scheme 1. Addition of an alkyllithium solution such as n-butyllithium in hexanes to an aryl or heteroaryl halide $(R^3)_4$A-X (X=Br, I) in an aprotic solvent such as THF at reduced temperatures provides the aryllithium or heteroaryllithium species $(R^3)_4$A-Li (2) Reaction of 2 with a ketone or aldehyde $R^1C(O)R^2$ in an aprotic solvent such as THF at reduced temperatures provides the corresponding alcohol 3. Reaction of the alcohol with a phenol in presence of an acid such as p-toluenesulfonic acid for 0.5 to 16 h, usually at elevated temperatures, provides the phenol intermediate 4. In some cases, extremely strong acids such as trifluoromethanesulfonic acid must be employed for the alkylation to occur (D. Klumpp et al, *J. Org. Chem.* 1999, 64, 6702). The phenolic group may then be converted to the triflate 5 by reaction with trifluoromethanesulfonic anhydride in an aprotic solvent such as DCM in presence of a base such as pyridine at reduced temperatures for 0.5 to 16 h. Reaction of the trifluoromethanesulfonate under a CO atmosphere in presence of a catalyst such as $PdCl_2(dppf)$, dichloromethane adduct and a base such as DIEA in an alcohol solvent such as MeOH or BuOH at elevated temperatures for 1 to 24 h provides the corresponding alcohol ester 1.

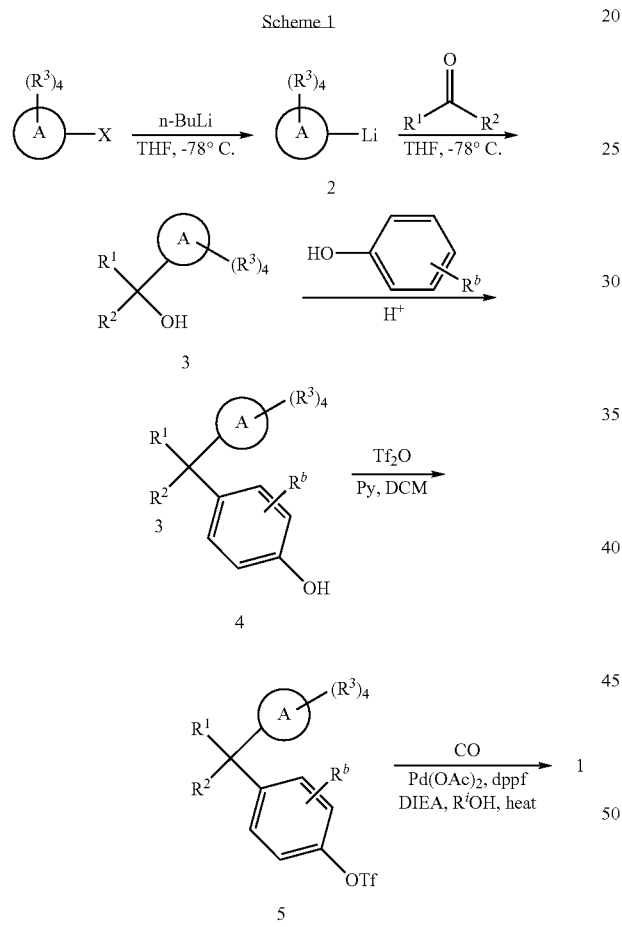

An alternative approach to intermediates 1 where $R^2$=H is shown in Scheme 2. Reaction of the aryllithium or heteroaryllithium species 2 with a 4-formyl benzoate 6 in an aprotic solvent such as THF at −78° C. for 0.5 to 8 h provides benzyl alcohol 7. Reaction of 7 with an allylsilane compound such as, for example, allyltrimethylsilane in presence of a metal such as titanium(IV) chloride in a solvent such as DCM at reduced temperatures for 0.5 to 8 h (Oku, A.; Harada, T.; Homoto, Y.; *Chem Lett* 1986, 1495) provides the corresponding allylic compound 1b.

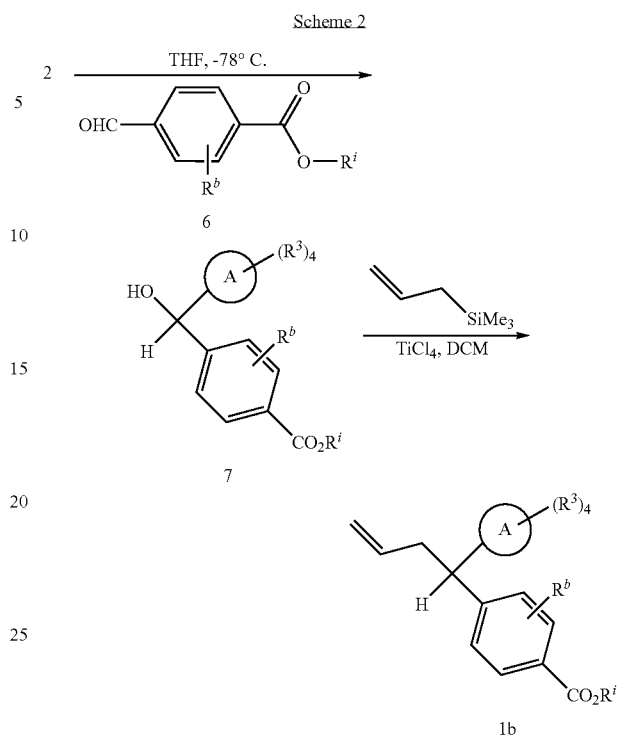

Another procedure for obtaining intermediates 1 where $R^2$=H is shown in Scheme 3. Alcohol 7 may be readily reduced to provide compound 8, for example by treatment with TFA and triethylsilane in chloroform for 0.5 to 48 h. Treatment of 8 with a base such as LHMDS in an aprotic solvent such as TH at reduced temperatures in presence of an activated halide such as a benzyl bromide as shown in the Scheme provides alkylated compound 1c.

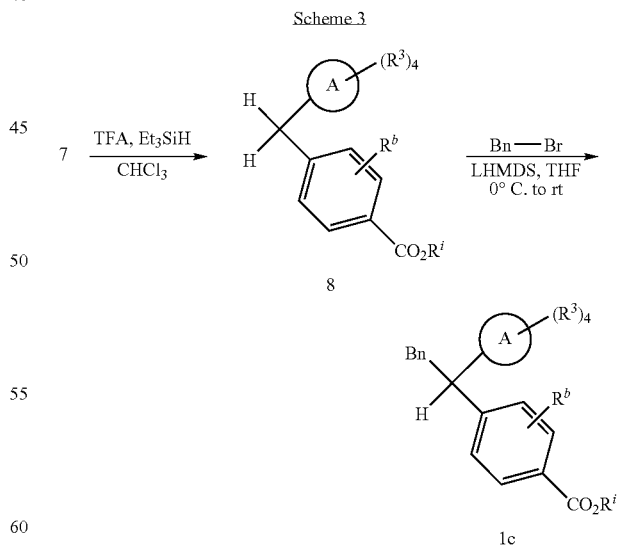

Conversely, intermediates 1 can be prepared via ketone intermediates such as 11. Such intermediates can be formed by various methods by those skilled in the art. One such approach is shown in Scheme 4 in which lithium salt 2 is reacted with 4-benzyloxybenzaldehyde to provide benzylic alcohol 10. Oxidation of 10, for example by treatment with 4-methylmorpholine N-oxide and tetrapropylammonium perruthenate in presence of 4A molecular sieves in DCM at 0° C. (Griffith, W. P.; Ley, S. V. *Aldrichimica Acta* 1990, 23, 13), provides ketone 11. Reaction of 11 with a Grignard complex $R^1MgBr$ gives the tertiary alcohol 12, which can be reduced to afford intermediate 13 using TFA and triethylsilane in DCM. Removal of the benzyl group by hydrogenolysis with a catalyst such as 10% Pd/C provides the phenol 14 which can be converted to the ester 1d via the triflate, as outlined in Scheme 1 (vide supra).

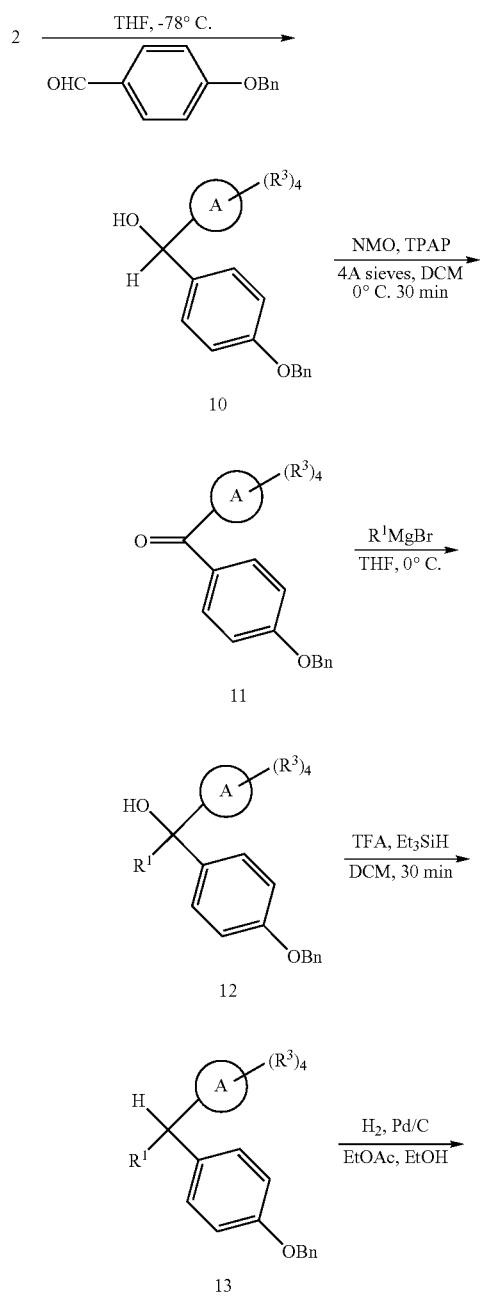

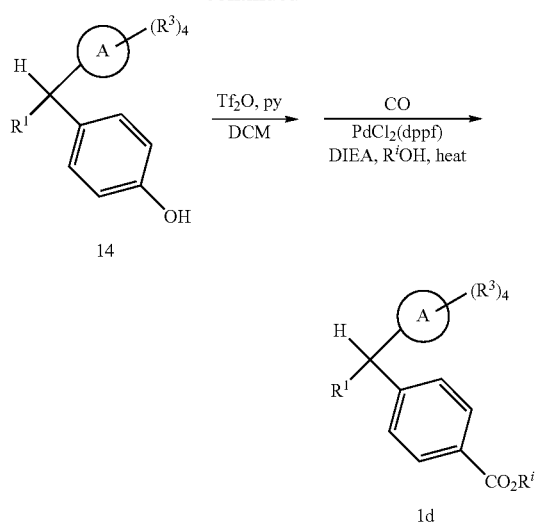

Another approach to intermediates 1 involves construction of ring A in the presence of $R^1$ and $R^2$. One such example is depicted in Scheme 5 and involves alkylation of tert-butyl (4-carbomethoxyphenyl)acetate 15 with $R^1$—Br in presence of a base such as NaH in a polar solvent such as DMF to provide ester 16. Removal of the tert-butyl group under acidic conditions provides carboxylic acid 17 which can readily be converted to various fused heterocycles, for example by reaction with the appropriate ortho-substituted aniline, such as a phenylenediamine as shown in Scheme 5 which provides the benzimidazole 1e.

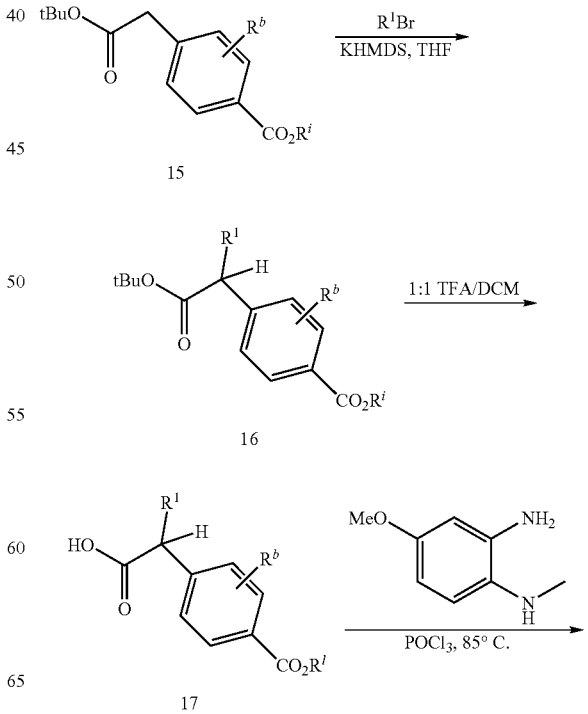

-continued

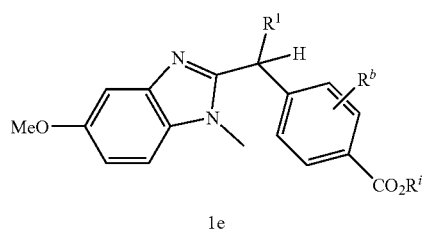

1e

Ester intermediates 1 may readily be converted to final products I using methods known to those skilled in the art. Shown in Scheme 6, saponification of the ester 1 may be achieved using a base such as aqueous lithium- or sodium hydroxide in a polar solvent such as tetrahydrofuran, dioxane, methanol, ethanol or a mixture of similar solvents to provide carboxylic acid 19. The acid may then be elaborated with the appropriate amine $H_2NR^a$ using a coupling reagent such as 1-ethyl-3-(3-dimethylaminopropyl)-carbodiimide (EDC) and 1-hydroxybenzotriazole (HOBt), or benzotriazole-1-yloxytrispyrrolidino-phosphonium hexafluorophosphate (PyBOP) and a base, generally diisopropylethylamine, in a solvent such as N,N-dimethylformamide (DMF) or methylene chloride for 0.5 to 48 h at ambient or slightly elevated temperatures. For compounds I where $Ra=\!\!=\!\!-CH_2CH_2CO_2R^4$ or $-CH_2CH(OH)CO_2R^4$, and $R^4=\!C_{1-6}$alkyl, the ester may be readily cleaved to provide the carboxylic acid ($R^4=\!H$) by treatment with a base such as aqueous lithium or sodium hydroxide in a polar solvent such as tetrahydrofuran, dioxane, methanol, ethanol or a mixture of similar solvents at ambient or elevated temperatures. Additionally, when $R^4$ is a tert-butyl group it is conveniently removed by treatment with an acid such as trifluoroacetic acid, commonly as a 1:1 mixture with methylene chloride, for 0.5 to 8 h at ambient temperature.

Scheme 6

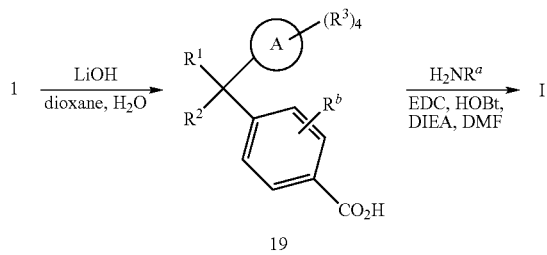

As will be known to those skilled in the art, in all schemes, the product I and all synthetic intermediates may be purified from unwanted side products, reagents and solvents by recrystallization, trituration, preparative thin layer chromatography, flash chromatography on silica gel as described by W. C. Still et al, *J. Org. Chem.*, 1978, 43, 2923, or reverse-phase HPLC. Compounds purified by HPLC may be isolated as the corresponding salt.

Additionally, in some instances intermediate 1, previous or subsequent intermediates, or final compound I may be comprised of a mixture of enantiomers or diastereomers. As will be known to those skilled in the art, such enantiomers and diastereomers may be separated by various methods including crystallization, chromatography using a homochiral stationary phase and, in the case of diastereomers, normal-phase and reverse-phase chromatography.

In some cases, the product I, the benzoate ester 1 and other intermediates from the reactions described in the schemes will be further modified. These manipulations may include, but are not limited to, substitution, reduction, oxidation, alkylation, acylation, and hydrolysis reactions, which are commonly known to those skilled in the art.

For example, shown in Scheme 7, an aromatic or heteroaromatic hydroxyl group $A(R^3)_3OH$ of intermediates such as 1f may be readily alkylated with an alkyl- or benzyl halides $R^{ii}WX$ (X=Cl, Br or I) in a solvent such as DMF and a base such as $K_2CO_3$ or $CsCO_3$ at ambient or elevated temperatures to provide the corresponding ether 1g. Such ethers may also be readily prepared under Mitsunobu conditions, involving reaction of the aromatic hydroxyl group A-OH with the corresponding alkyl or benzyl alcohol $R^{ii}OH$ in an aprotic solvent such as DCM or THF in presence of a phosphine such as triphenylphosphine and an azadicarbonyl compound such as DIAD (O. Mitsunobu, *Synthesis* 1981, p. 1). The ether 1g may then be carried on to final products as described in Scheme 5 (vide supra), involving saponification of the ester to give acid 19a, then coupling of the acid to the desired amine such as β-alanine tert-butyl ester as shown in Scheme 7 to provide amido ester Ib, followed by deprotection if desired to provide the final product Ic. Also depicted in Scheme 7, the order of reactions may be reversed, with ester 1f first being converted to amide Ia using the procedures outlined in Scheme 6 (vide supra), followed by alkylation of the phenolic group to give ether intermediate Ib. Again, the tert-butyl group may be removed is so desired to provide carboxylic acid Ic.

Scheme 7

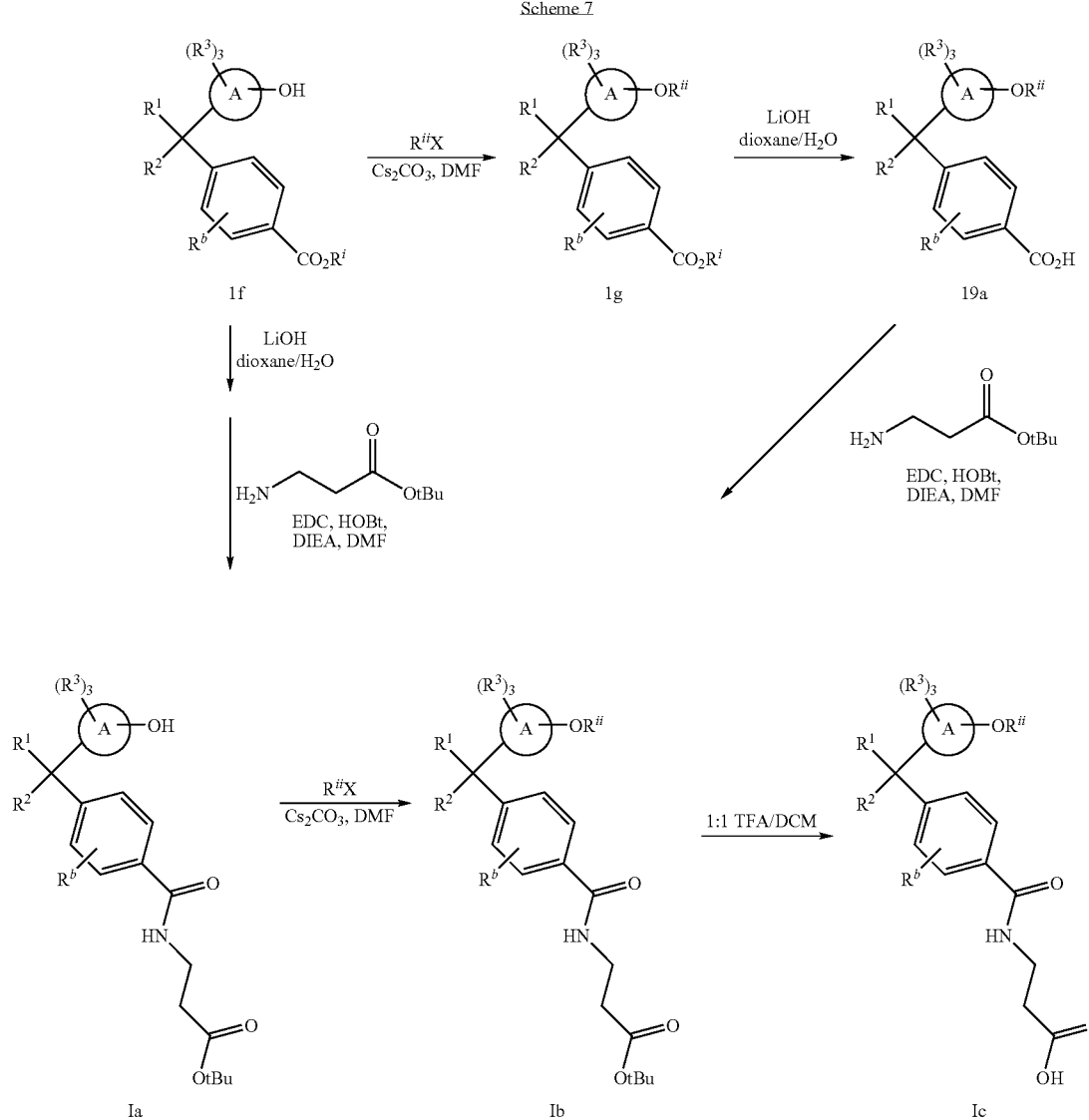

Shown in Scheme 8, $A(R^3)_3OH$ ester 1f may be converted to the trifluoromethanesulfonate 1h by reaction with trifluoromethanesulfonic anhydride in the presence of a base such as pyridine in an aprotic solvent such as DCM. The trifluoromethanesulfonate may be further elaborated using procedures known to those skilled in the art. For example, reaction of 1h with aryl-, heteroaryl-, alkyl- or alkenylboronic acids $R^{iii}$—$B(OH)_2$ in the presence of a catalyst such as palladium acetate and ligand such as tri-o-tolylphosphine and a base such as cesium carbonate in a solvent such as toluene at elevated temperatures for 0.5 to 16 h provides the corresponding carbon-linked compounds II (A. Suzuki, *J. Organomet. Chem.* 1999, 576, 147). Aryl and heteroaryltrifluoromethanesulfonates such as 1h may also be coupled to heteroatomic species including amines, amides, alcohols, phenols, thiols and nitrogenous heterocycles to provide the corresponding heteroatom-linked species (S. Ley and A. Thomas, *Angew.*

*Chem. Int. Ed.* 2003, 42, 5400). For example, also shown in Scheme 8, reaction of aryl triflate 1h with an alkyl or aryl thiol $HSR^{iv}$ in presence of a catalyst such as $Pd_2$ $dba_3$, a ligand such as Xantphos and a base such as DIEA in an aprotic solvent such as toluene at elevated temperatures provides the thioether 1j (*Org. Lett.* 2004, 6, 4587-4590). The thioether may then be oxidized if desired to the sulfoxide or sulfone using an oxidant such as MCPBA. Intermediates 1i, and 1j may then be carried on to final products I as described in Scheme 6 (vide supra).

Similarly, amido ester Ia may also be converted to trifluoromethanesulfonate intermediate 20 by reaction with trifluoromethanesulfonic anhydride in the presence of a base such as pyridine in an aprotic solvent such as DCM at reduced temperatures; the trifluoromethanesulfonate may then be analogously modified to provide the corresponding compounds Id and Ie.

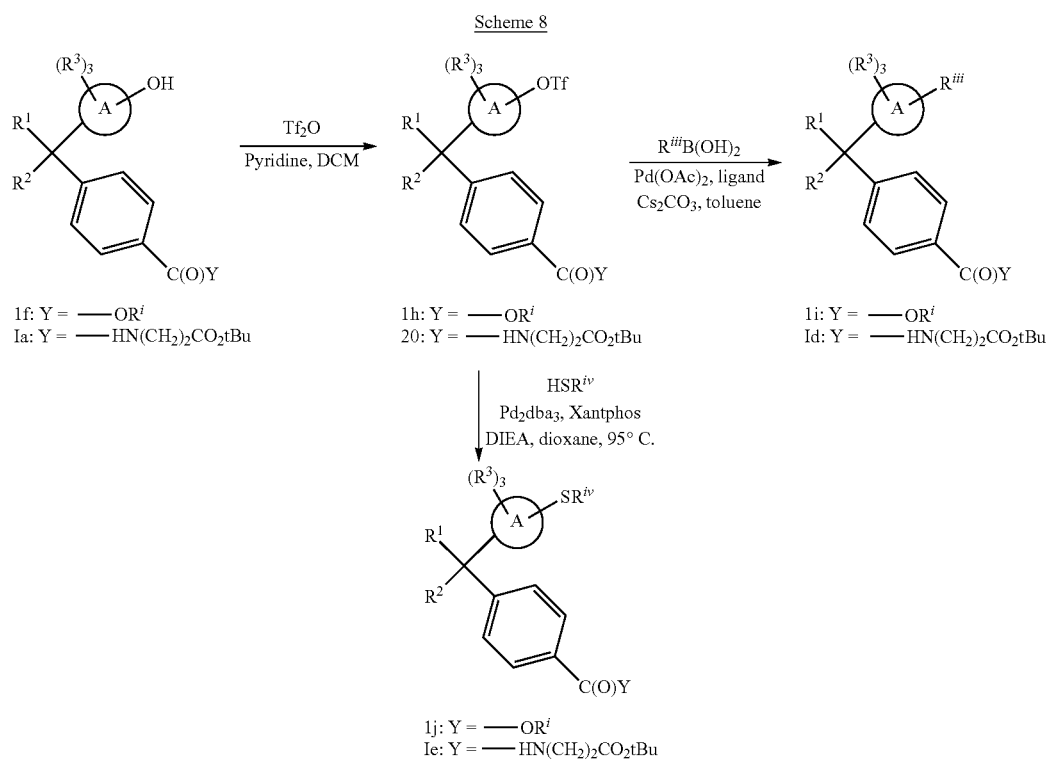

Scheme 8

1f: Y = —OR$^i$
1a: Y = —HN(CH$_2$)$_2$CO$_2$tBu

1h: Y = —OR$^i$
20: Y = —HN(CH$_2$)$_2$CO$_2$tBu

1i: Y = —OR$^i$
1d: Y = —HN(CH$_2$)$_2$CO$_2$tBu

1j: Y = —OR$^i$
1e: Y = —HN(CH$_2$)$_2$CO$_2$tBu

Hydroxyaromatic groups A(R$^3$)$_3$OH may also be readily halogenated. For example, when A(R$^3$)$_3$OH is a hydroxynaphthyl group as in 1k depicted in Scheme 9, the naphthyl group can be dichlorinated to provide 1l by treatment SO$_2$Cl$_2$ in a solvent such as DCM at 50° C. for 1-16 h (*Org. Synth.* 1955, p. 267). Hydroxynaphthyl compound 1k can also be selectively iodinated by treatment with benzyltrimethylammonium dichloroiodate in a mixture of MeOH and DCM to provide 1n (*Heterocycles,* 2002, 56, 465). The iodide may then be further elaborated with various groups by those skilled in the art. As an example, also depicted in Scheme 8, the iodide can be converted to a cyano group to provide 1n by treatment with Zn(CN)$_2$ in presence of a catalyst such as Pd(Ph$_3$P)$_4$ in a solvent such as DMF at elevated temperatures for 0.5-8 h (*Tetrahedron Lett.* 1999, 40, 8193). The hydroxyl group may then be elaborated as outlined in Schemes 7 and 8.

Scheme 9

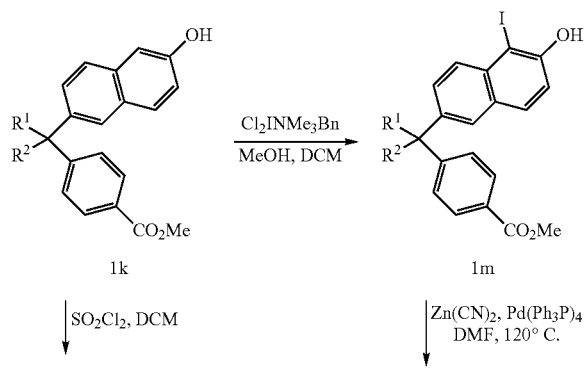

-continued

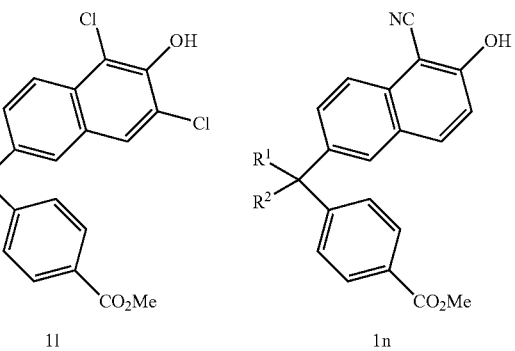

The R$^1$ and R$^2$ groups may also be elaborated. As shown in Scheme 10, allyl compound 1b, for example, may be reduced to give the propyl derivative 1o using a catalyst such as 10% Pd/C in a solvent such as EtOAc or EtOH or a mixture of such solvents under an atmosphere of H$_2$ for 0.5-16 h. The allyl group may also undergo metathesis reactions with alkenes (*J. Am. Chem. Soc.* 2003, 125, 11360) such as H2CCR$^{vi}$R$^{vii}$ in presence of a catalyst such as Zhan catalyst I (Zannan Pharma Ltd.) in a solvent such as DCM to provide the corresponding alkene 1p, which if so desired may be reduced to the alkane 1q by hydrogenation under an H$_2$ atmosphere in presence of a catalyst such as 10% Pd/C in a solvent such as EtOAc or EtOH or a mixture thereof. All products thus derived from 1b may be carried on to final products of formula I as described in Scheme 6 (vide infra).

Scheme 10

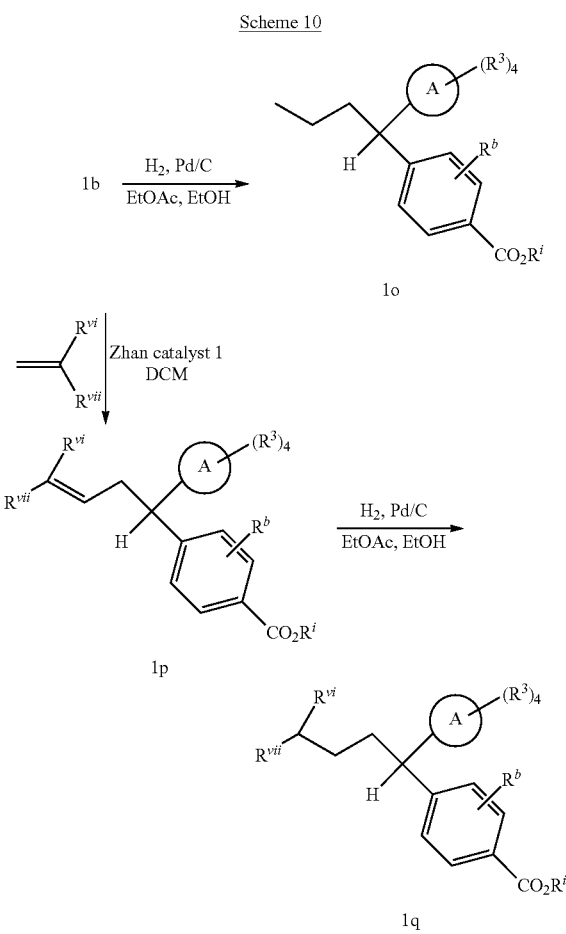

General Experimental: Chemical reactions were monitored by LC-MS, and the purity and identity of the reaction products were assayed by LC-MS using one of the following conditions:

Method A (LCMS A): Column: Waters Xterra C18 (3.0×50 mm). Gradient: 10-100% CH$_3$CN (containing 0.05% TFA)/H$_2$O (containing 0.06% TFA) over 3.75 min@1 mL/min Method B (LCMS B): Column: MetaChem Polaris (4.6×50 mm). Gradient: 5-95% CH$_3$CNtH$_2$O, (both with 0.05% TFA) over 2.5 min@2.5 mL/min Method C (LCMS C): Column: Waters Xterra C18 (3.0×50 mm). Gradient: 10-98% CH$_3$CN (containing 0.05% TFA)/H$_2$O (containing 0.06% TFA) over 3.25 min@1.5 mL/min Method D (LCMS D): Column: Waters Xterra C18 (3.0×50 mm). Gradient: 10-98% CH$_3$CN (containing 0.05% TFA)/H$_2$O (containing 0.06% TFA) over 1.25 min@1.5 mL/min Method E (LCMS E): Column: Waters Xterra C18 (3.0×50 mm). Gradient: 10-100% MeCN (containing 0.05% formic acid)/H$_2$O (containing 0.06% formic acid) over 3.75 min@1 mL/min Preparative HPLC was performed on either a YMC-Pack Pro C18 column (150×20 mm i.d.) or a Kromasil 100-10C8 column (100×30 mm i.d.) at an initial flow rate of 4 mL/min for 1.35 min, followed by 20 mL/min for 10.6 min. The gradients employed during the faster part of the run are described, and all runs were followed with 100% organic at 20 mL/min for 0.5 min.

Flash chromatography on silica gel was performed using pre-packed silica gel columns on a Biotage Horizon or Biotage SP-1 instrument equipped with a UV detector using the gradients described in the experimental section.

Chiral resolutions were performed using the column (250× 20 mm i.d.) and mobile phase (flow rate=9 mL/min) described in the text. Where two enantiomers were obtained, data for the enantiomer corresponding to one of the enantiomers is provided.

The following examples are provided so that the invention might be more fully understood. They should not be construed as limiting the invention in any way.

EXAMPLE 1

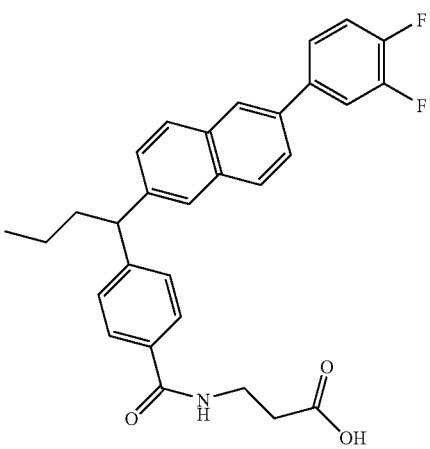

Step A: Methyl 4-[(RS)-hydroxy(6-methoxy-2-naphthyl)methyl]benzoate n-BuLi (4.4 mL of a 2.5 M solution in hexanes, 11 mmol) was added dropwise to a solution of 6-methoxy-2-bromonaphthalene (2.4 g, 10 mmol) in 80 mL of THF cooled in dry ice-acetone bath. After aging for 15 min, the cold mixture was quickly cannulated to a stirring mixture of methyl 4-formylbenzoate (1.64 g, 10 mmol) in 20 mL of THF cooled in dry ice-acetone bath. After stirring for an additional 15 min, the reaction mixture was poured into a mixture of aq ammonium chloride, hexanes and EtOAc. The organic phase was separated, concentrated and purified by flash chromatography on silica gel (mobile phase=10% to 30% EtOAc in hexanes) to give the title compound as a racemic mixture.

$^1$H NMR (500 MHz, CDCl$_3$): δ (ppm) 8.02 (d, J=8.5 Hz, 2H), 7.77 (s, 1H), 7.72 (t, J=9.5 Hz, 2H), 7.52 (d, J=8.2 Hz, 2H), 7.38 (dd, J=8.5, 1.6 Hz, 1H), 7.17 (dd, J=8.9, 2.5 Hz, 1H), 7.12 (d, J=2.3 Hz, 1H), 6.01 (s, 1H), 3.93 (s, 3H), 3.91 (s, 3H).

Step B: Methyl 4-[1(RS)-1-(6-methoxy-2-naphthylbut-3-en-1-yl]benzoate

A solution of title compound from the previous step (5.2 g, 16 mmol), titanium(IV) chloride (35 mL of a 1 M solution in DCM, 35 mmol) and allyltrimethylsilane (12.5 mL, 79 mmol) in 120 mL of DCM was warmed from −78° C. to −30° C. over 2.5 h. The mixture was cooled to −78° C. and the reaction was quenched by addition of water, hexanes and EtOAc. After warming to ambient temperature, the organic phase was separated, concentrated and purified by flash chromatography on silica gel (mobile phase=5% to 15% EtOAc in hexanes) to give the title compound as a racemic mixture.

$^1$H NMR (500 MHz, CD$_2$Cl$_2$): δ (ppm) 7.96 (d, J=8.5 Hz, 2H), 7.71 (m, 2H), 7.67 (s, 1H), 7.40 (d, J=8.2 Hz, 2H), 7.32 (dd, J=8.5, 1.8 Hz, 1H), 7.15 (m, 2H), 5.79 (m, 1H), 5.08 (m, 1H), 4.98 (m, 1H), 4.24 (t, J=8.0 Hz, 1H), 3.91 (s, 3H), 3.88 (s, 3H), 2.95 (m, 1H).

Step C: tert-Butyl-N-{4-[(1R)-1-(6-hydroxy-2-naphthyl)but-3-en-1-yl]benzoyl}-β-alaninate and tert-Butyl-N-{4-[(1S)-1-(6-hydroxy-2-naphthyl)but-3-en-1-yl]benzoyl}-β-alaninate To the title compound of the previous reaction (2.54 g, 7.36 mmol) in 40 mL of dichloromethane at 0° C. was added BBr$_3$ (22 mL of a 1M solution in dichloromethane, 22 mmol). After 2 h, the cold reaction mixture was quenched with 50 mL of water and 200 mL of EtOAc. The organic phase was separated, concentrated and treated with a mixture consisting of 25 mL each of 1,4-dioxane, MeOH and 3 N NaOH, at 50° C. for 25 min. The reaction mixture was acidified with 1 N HCl and extracted twice with EtOAc. The organic phase was concentrated and the residue was taken up in 40 mL of DMF, then treated with β-alanine tert-butyl ester hydrochloride (2.64 g, 14.5 mmol), HOBt (2.23 g, 16.5 mmol), EDC (2.78 g, 14.5 mmol) and DIEA (4.8 mL, 27.6 mmol). After 1 h at 45° C., the reaction mixture was cooled and partitioned between 300 mL of water and 300 mL of 1:1 hexanes/EtOAc. The aqueous phase was extracted with dichloromethane. The combined organic phase was concentrated and purified by flash chromatography on silica gel (mobile phase: 33% to 60% EtOAc/hexanes) to give the product as a racemic mixture. LCMS (ESI): m/z 390.1 [M-tert-Bu+H]$^+$.

The enantiomers were resolved by chiral HPLC on a ChiralPak-IA column using 30% isopropyl alcohol in n-heptane as the mobile phase to give Enantiomer A as the faster-eluting product and Enantiomer B as the slower eluting product.

$^1$H NMR (500 MHz, CD$_2$Cl$_2$): δ (ppm) 7.71 (m, 3H), 7.65 (s, 1H), 7.56 (d, J=8.5 Hz, 1H), 7.38 (d, J=8.1 Hz, 2H), 7.27 (dd, J=8.6, 1.7 Hz, 1H), 7.11 (m, 2H), 6.84 (br m, 1H), 5.79 (m, 1H), 5.09 (m, 1H), 4.98 (m, 1H), 4.22 (t, J=7.9 Hz, 1H), 3.66 (q, 2H), 2.93 (m, 2H), 2.55 (t, J=6.1 Hz, 2H), 1.46 (s, 9H).

Step D: tert-Butyl-N-(4-{(1R or S)-1-[6-(3,4-difluorophenyl)-2-naphthyl]but-3-en-1-yl}benzoyl)-β-alaninate To a stirring solution of Enantiomer B from the previous reaction (375 mg, 0.84 mmol) and pyridine (0.16 mL, 2.0 mmol) in 8 mL of dichloromethane at −78° C. was added trifluoromethanesulfonic anhydride (0.16 mL, 0.98 mmol). The cold bath was removed and the reaction mixture was allowed to warm for 10 min. The reaction mixture was cooled back to −78° C. and quenched with water-hexanes-EtOAc. The organic phase was collected and the aqueous phase was washed with dichloromethane. The combined organic phase was passed through a pad of silica gel and the filtrate was concentrated to provide the crude triflate. A portion of the triflate (100 mg, 0.17 mmol), 3,4-difluorophenylboronic acid (41 mg, 0.26 mmol), tetrakis(triphenylphosphine) palladium (0) (17 mg, 0.015 mmol) and triethylamine (0.06 mL) were combined in 1.7 mL of ethylene glycol dimethyl ether and heated in a sealed tube at 125° C. for 15 min. The reaction mixture was cooled, concentrated and purified by flash chromatography on silica gel (mobile phase=20% to 25% (v/v) EtOAc in hexanes) to provide the title compound.

$^1$H NMR (500 MHz, CD$_2$Cl$_2$): δ (ppm) 7.97 (s, 1H), 7.90 (d, J=8.5 Hz, 1H), 7.84 (d, J=8.5 Hz, 1H), 7.77 (s, 1H), 7.69 (m, 3H), 7.55 (m, 1H), 7.47 (m, 1H), 7.39 (m, 3H), 7.30 (m, 1H), 6.75 (br, 1H), 5.79 (m, 1H), 5.09 (m, 1H), 4.99 (m, 1H), 4.28 (t, J=7.8 Hz, 1H), 3.63 (q, 2H), 2.96 (m, 2H), 2.52 (t, J=6.1 Hz, 2H), 1.45 (s, 9H).

Step E: N-(4-{(1R or S)-1-[6-(3,4-Difluorophenyl)-2-naphthyl]but-3-en-1-yl}benzoyl)-β-alanine The product of the previous reaction (5.3 mg, 0.01 mmol) and 10% Pd/C (3 mg) were stirred in a mixture of 0.2 mL of EtOAc and 0.05 mL of EtOH under hydrogen (balloon) for 2 h. The solid was removed by filtration. The filtrate was concentrated and the residue was treated with 1:1 TFA/CH$_2$Cl$_2$ until LC-MS showed the complete cleavage of the tert-butyl ester. The solvent was removed and the residue was purified by reverse phase HPLC (YMC-C18 column, gradient=45% to 100% MeCN/H$_2$O, both containing 0.1% TFA) to provide the title compound. LCMS (ESI): m/z 488.3 [M+1]$^+$.

$^1$H NMR (500 MHz, acetone-d$_6$): δ (ppm) 8.17 (s, 1H), 8.00 (d, J=8.7 Hz, 1H), 7.93 (m, 2H), 7.84 (m, 3H), 7.77 (m, 2H), 7.65 (m, 1H), 7.49 (m, 4H), 4.27 (t, J=7.8 Hz, 1H), 3.63 (q, 2H), 2.65 (t, J=6.8 Hz, 2H), 2.22 (m, 2H), 1.36 (m, 2H), 0.98 (t, J=7.3 Hz, 3H).

EXAMPLE 2

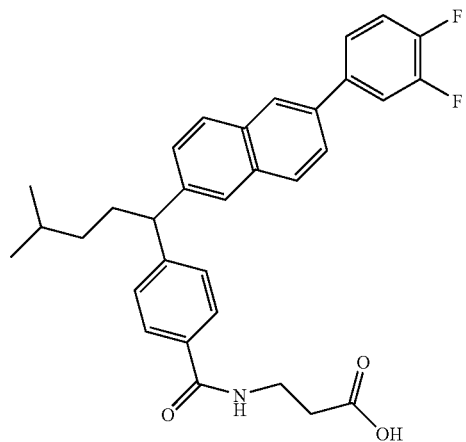

Step A: N-(4-{1(R or S)-1-[6-(3,4-Difluorophenyl-2-naphthyl]-4-methylpentyl}benzoyl)-β-alanine A mixture of the title compound from Example 1, Step D (8.8 mg, 0.016 mmol), 1 mg of Zhan catalyst I (Zannan Pharma Ltd., 1 mg, 0.0015 mmol) and 2-methyl-2-butene (0.3 mL, 2.8 mmol) in 0.3 mL of dichloromethane was stirred at ambient temperature for 2.5 h. Baseline material was removed using preparative thin layer chromatography (mobile phase 3:1 (v/v) hexanes:EtOAc). The resulting product was stirred under a hydrogen atmosphere (balloon) with catalytic Pd black in a mixture of EtOAc and EtOH for 3 h. The crude reaction mixture was filtered and the filtrate was concentrated in vacuo. The residue was treated with 1:1=TFA/dichloromethane for 30 min. The solvent was removed and crude material was purified by reverse phase HPLC (YMC- C18 column, gradient=45% to 100% MeCN/H₂O, both containing 0.1% TFA) to provide the title compound. LCMS (ESI): m/z 516.3 [M+1]⁺. ¹H NMR (500 MHz, acetone-d₆): δ (ppm) 8.17 (s, 1H), 8.00 (d, J=8.7 Hz, 1H), 7.93 (m, 2H), 7.83 (m, 3H), 7.77 (m, 2H), 7.66 (m, 1H), 7.49 (m, 4H), 4.21 (t, J=7.8 Hz, 1H), 3.63 (q, 2H), 2.65 (t, J=6.9 Hz, 2H), 2.25 (m, 2H), 1.65 (m, 1H), 1.24 (q, 2H), 0.90 (d, J=6.6 Hz, 6H).

EXAMPLE 3

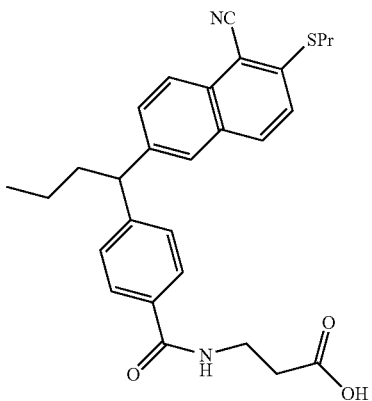

Step A: tert-Butyl N-{4-[(1R or S)-1-(6-hydroxy-2-naphthyl)butyl]benzoyl}-β-alaninate To a solution of the Enantiomer B from Example 1, Step C (192 mg, 0.43 mmol) in 10 mL of MeOH was added a catalytic amount of 20% palladium hydroxide on carbon. The reaction was stirred under H₂ (balloon) for over 2 h. The reaction was filtered through celite and the filter cake was washed with MeOH. The combined filtrate and washings were concentrated under reduced pressure to afford the product as a yellow solid. LC-MS (ESI): m/z=448.2 [M+1]⁺.

Step B: tert-Butyl-N-{4-[(1R or S)-1-(6-hydroxy-5-iodo-2-naphthyl)butyl]benzoyl}-β-alaninate A mixture of the title compound from the previous reaction (10 mg, 0.022 mmol), calcium carbonate (4.5 mg, 0.04 mmol) and benzyltrimethylammonium dichloroiodate (9 mg, 0.03 mmol) in 0.3 mL of 1:1 (v/v) MeOH/DCM was stirred for 24 h. The solid was removed by filtration and the filtrate was concentrated and purified by reverse phase HPLC (YMC-C18 column, gradient=45% to 100% MeCN/H₂O, both containing 0.1% TFA) to provide the title compound. LCMS (ESI): m/z 596.0 [M-tert-Bu+Na]⁺. ¹H NMR (500 MHz, CD₂Cl₂): δ (ppm) 7.88 (d, J=8.9 Hz, 1H), 7.73 (d, J=8.7 Hz, 1H), 7.70 (d, J=8.5 Hz, 2H), 7.66 (d, J=1.4 Hz, 1H), 7.41 (m, 3H), 7.25 (d, J=8.7 Hz, 1H), 7.07 (t, 1H), 4.17 (t, J=7.7 Hz, 1H), 3.68 (q, 2H), 2.57 (t, J=6.1 Hz, 2H), 1.47 (s, 9H), 2.16 (m, 2H), 1.34 (m, 2H), 0.98 (t, J=7.3 Hz, 3H).

Step C: tert-Butyl-N-{4-[(1R or S)-1-(5-cyano-6-hydroxy-2-naphthyl)butyl]benzoyl}-β-alaninate The title compound from the previous reaction (9 mg, 0.016 mmol), Zn(CN)₂ (8 mg, 0.07 mmol) and Pd(PPh₃)₄ (6.3 mg, 0.005 mmol) were heated in 0.2 mL of DMF in a capped vial at 120° C. for 1 h 20 min. The crude material was purified by reverse phase HPLC (YMC-C18 column, gradient=45% to 100% MeCN/H₂O, both containing 0.1% TFA) to yield the title compound. LCMS (ESI): m/z 417.2 [M-tert-Bu+H]⁺. ¹H NMR (500 MHz, CD₂Cl₂): δ (ppm) 7.93 (d, J=8.5 Hz, 1H), 7.85 (d, J=8.9 Hz, 1H), 7.71 (d, J=8.2 Hz, 2H), 7.67 (s, 1H), 7.50 (dd, J=8.7, 1.6 Hz, 1H), 7.38 (d, J=8.2 Hz, 2H), 7.20 (d, J=8.2 Hz, 1H), 7.10 (t, 1H), 4.14 (t, J=7.8 Hz, 1H), 3.70 (q, 2H), 2.58 (t, J=5.9 Hz, 2H), 2.14 (m, 2H), 1.47 (s, 9H), 1.31 (m, 2H), 0.96 (t, J=7.3 Hz, 3H).

Step D: N-{4-[(1R or S)-1-(5-Cyano-6-propylthio-2-naphthyl)butyl]benzoyl}-β-alanine To a solution of the title compound from the previous reaction (6.5 mg, 0.016 mmol) and pyridine (10 mg, 0.13 mmol) in 8 mL of dichloromethane cooled to −78° C. was added trifluoromethanesulfonic anhydride (12 mg, 0.042 mmol). The bath was removed and the reaction mixture was allowed to warm for 10 min. The reaction was cooled to −78° C. and quenched with water-hexane-EtOAc. The organic phase was collected and the aqueous phase was washed with dichloromethane. The combined organic phase was passed through a pad of silica gel and the filtrate was concentrated in vacuo to provide the crude triflate. The triflate thus obtained was combined with Pd₂dba₃ (1 mg), Xantphos (1.3 mg), DIEA (0.014 mL) and propanethiol (0.007 mL) in 0.2 mL of 1,4-dioxane. The solution was heated in a capped vial for 35 min at 120° C. The reaction mixture was concentrated and the residue was treated with 2 mL of 1:1 (v/v) TFA/dichloromethane for 35 min. The crude material was concentrated and purified by reverse phase TALC (YMC-C18 column, gradient=45% to 100% MeCN/H₂O, both containing 0.1% TFA) to provide the title compound. LCMS (ESI): m/z 475.1 [M+1]⁺.

¹H NMR (500 MHz, acetone-d₆): δ (ppm) 8.16 (d, J=8.7 Hz, 1H), 8.00 (m, 2H), 7.83 (d, J=8.2 Hz, 2H), 7.78 (m, 1H), 7.72 (m, 2H), 7.47 (d, J=8.4 Hz, 2H), 4.28 (t, J=7.8 Hz, 1H), 3.62 (q, 2H), 3.22 (t, J=7.3 Hz, 2H), 2.64 (t, J=6.9 Hz, 2H), 2.20 (m, 2H), 1.74 (m, 2H), 1.33 (m, 2H), 1.07 (t, J=7.3 Hz, 3H), 0.96 (t, J=7.3 Hz, 3H).

EXAMPLE 4

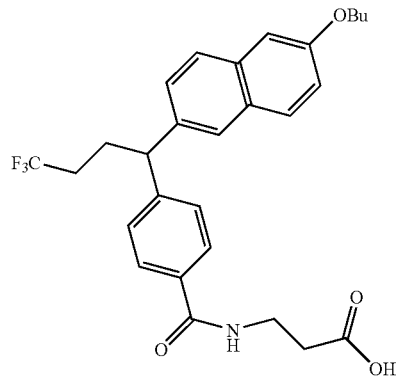

Step A: (1RS)-4,4,4-Trifluoro-1-(6-methoxy-2-naphthyl)butan-1-ol

To a cold (−78° C.) anhydrous solution of 2-methoxy-6-bromonaphthylene (7.8 g, 28.5 mmol) in THF (100 mL) was added n-BuLi (12.4 mL of a 2.5 M solution in hexanes, 31 mmol). The mixture was stirred at −78° C. under a nitrogen atmosphere for 15 min, then 4,4,4-trifluorobutylaldehyde (3.0 g, 24 mmol) was added slowly to the reaction mixture. The bath was allowed to warm to room temperature and the reaction mixture was quenched with saturated NH$_4$Cl (aq). The resultant mixture was extracted with EtOAc/hexanes. The organic layer was evaporated in vacuo and the crude residue was purified by flash chromatography on silica gel (gradient elution, 0% to 25% EtOAc/hexanes, 795 mL; 25% to 60% EtOAc/hexanes, 1575 mL) to provide the title compound as a racemic mixture. $^1$H NMR (500 MHz, CDCl$_3$): δ 7.81-7.72 (m, 3 H), 7.46 (dd, J=8.5, 1.8 Hz, 1 H), 7.20 (dd, J=8.9, 2.5 Hz, 1 H), 7.17 (s, 1 H), 4.94-4.90 (m, 1H), 3.96 (s, 3 H), 2.38-2.04 (m, 4 H).

Step B: 4-[(1RS)-4,4,4-Trifluoro-1-(6-methoxy-2-naphthyl)butyl]phenol

The title compound from the previous step (5.0 g, 17.6 mmol) and phenol (2.5 g, 26.6 mmol) were combined and heated until molten. para-Toluenesulfonic anhydride (1.7 g, 8.9 mmol) was added and the mixture was stirred at 95° C. for 1 h. The reaction mixture was allowed to cool to room temperature and diluted with saturated NaHCO$_3$ (aq). The resultant slurry was extracted with EtOAc. The organic layer was concentrated in vacuo and purified by flash chromatography on silica gel (gradient elution, 0% to 35% EtOAc/hexanes, 500 mL; 35% to 75% EtOAc/hexanes, 2000 mL) to provide the title compound as a racemic mixture. $^1$H NMR (500 MHz, CD$_2$Cl$_2$): δ 7.75-7.64 (m, 3 H), 7.30 (dd, J=8.46, 1.8 Hz, 1 H), 7.19-7.13 (m, 4 H), 6.80 (d, J=8.46 Hz, 2 H), 4.02 (t, J=8.0 Hz, 1 H), 3.92 (s, 3 H), 2.46-2.30 (m, 2H), 2.19-2.05 (m, 2H).

Step C: Butyl 4-[(1RS)-4,4,4-trifluoro-1-(6-methoxy-2-naphthyl)butyl]benzoate

To a solution of the title compound from the previous step (3.78 g, 10.5 mmol) in anhydrous CH$_2$Cl$_2$ (60 mL) were added pyridine (1.27 mL, 15.8 mmol), followed by trifluoromethanesulfonic anhydride (2.12 mL, 3.55 g, 12.6 mmol). The mixture was stirred at room temperature for 20 min, quenched with water, and the resultant mixture was extracted with EtOAc/hexanes. The organic phase was washed with 1N HCl, and then passed through a short silica plug. The filtrate was concentrated to dryness to give the triflate as a solid. The triflate thus obtained was taken up in n-butanol (80 mL) and dichloro[1,1'-bis(diphenylphosphino)ferrocene]palladium (II), dichloromethane adduct (745 mg, 1.02 mmol) and DIEA (5.3 mL, 30.6 mmol) were added. The reaction mixture was stirred at 90° C. under a CO atmosphere (balloon) for 2 h. The resulting mixture was concentrated and purified by flash chromatography on silica gel (gradient elution, 0% to 25% EtOAc/hexanes, 450 mL; 25% to 70% EtOAc/hexanes, 2049 mL) to provide the title compound as a racemic mixture. LCMS (ESI): m/z=445.4 [M+H]$^+$. $^1$H NMR (500 MHz, CD$_2$Cl$_2$): δ 7.98 (dd, J=6.6, 1.6 Hz, 2 H), 7.74-7.65 (m, 3 H), 7.39 (d, J=8.4 Hz, 2 H), 7.32-7.27 (m, 1 H), 7.15-7.11 (m, 2 H), 4.29 (t, J=6.6 Hz, 2 H), 4.15 (t, J=7.8 Hz, 1 H), 3.91 (s, 3H), 2.50-2.35 (m, 2 H), 2.17-2.04 (m, 2 H), 1.73 (quint, J=6.6 Hz, 2 H), 1.48 (quint, J=7.3 Hz, 2 H). 0.98 (t, J=7.5 Hz, 3 H).

Step D: tert-Butyl-N-{4-[(1R)-4,4,4-trifluoro-1-(6-hydroxy-2-naphthyl)butyl]benzoyl}-β-alaninate and tert-Butyl-N-{4-[(1S)-4,4,4-trifluoro-1-(6-hydroxy-2-naphthyl)butyl]benzoyl}-β-alaninate To a cold (0° C.) solution of the title compound from the previous reaction (3.7 g, 8.3 mmol) in anhydrous CH$_2$Cl$_2$ (80 mL) under a nitrogen atmosphere was slowly added BBr$_3$ (24 mL of a 1.0 M solution in CH$_2$Cl$_2$, 24 mmol) via syringe. The mixture was stirred at 0° C. for 2 h and quenched with water. The mixture was extracted with EtOAc/hexanes and the organic layer was concentrated in vacuo. The residue was dissolved in 36 mL of a 1:1 (v/v) mixture of dioxane:MeOH, and NaOH (18 mL of a 3 N aq solution) was added. The mixture was stirred at 60° C. for 3 h, allowed to cool to rt, and acidified with 1 N aq HCl (60 mL). The aqueous phase was extracted with EtOAc and the organic phase was washed with brine, dried over anhydrous Na$_2$SO$_4$ and concentrated in vacuo to provide the carboxylic acid as a racemic mixture. LC/MS (ESI): m/z 375.2 [M+H]$^+$.

To the carboxylic acid thus obtained were added EDC (3.2 g, 16.7 mmol), HOBt (2.26 g, 16.7 mmol) and β-alanine tert-butyl ester hydrochloride (3.0 g, 16.7 mmol). The combined solids were dissolved in DMF (50 mL), DIEA (4.3 mL, 25 mmol) was added, and the reaction mixture was stirred at 50° C. for 1 h. The reaction mixture was quenched by addition of water and the aqueous phase was extracted with EtOAc/hexanes. The organic phase was washed with water and brine, dried over Na$_2$SO$_4$ and concentrated in vacuo. The crude residue was purified by silica gel chromatography (gradient elution, 0% to 25% EtOAc/hexanes, 306 mL; 25% to 75% EtOAc/hexanes, 2181 mL) to give a yellow solid: LCMS, m/z 524.3 [M+Na]$^+$. Chiral resolution (ChiralPak AD column, mobile phase=40:60 isopropanol:heptane) provided Enantiomer A as the faster-eluting product and Enantiomer B as the slower-eluting product.

$^1$H NMR (500 MHz, CD$_2$Cl$_2$): δ 7.74-7.69 (m, 3 H), 7.65 (s, 1 H), 7.59 (d, J=8.5 Hz, 1 H), 7.38 (d, J=8.5 Hz, 2 H), 7.25 (dd, J=8.5, 1.8 Hz, 1 H), 7.13-7.09 (m, 2 H), 6.85-6.78 (br m, 1 H), 6.00-5.93 (br s, 1 H), 4.13 (t, J=8.0 Hz, 1 H), 3.65 (quart, J=6.2 Hz, 2 H), 2.54 (t, J=6.2 Hz, 2 H), 2.49-2.36 (m, 2 H), 2.16-2.05 (m, 2 H), 1.46 (s, 9 H).

Step E: N-{4-[(1R)-4,4,4-Trifluoro-1-(6-hydroxy-2-naphthyl)butyl]benzoyl}-β-alanine and N-{4-[(1S)-4,4,4-Trifluoro-1-(6-hydroxy-2-naphthyl)butyl]benzoyl}-β-alanine The R and S enantiomers from the previous reaction (6 mg each) were separately stirred with 10 mg of cesium carbonate in 0.1 mL DMF containing 14% (v/v) of 1-iodobutane for 1 h 15 min at 45° C. The crude reaction mixtures were concentrated and the residues were each treated with 2 mL of 1:1 dichloromethane/TFA for 30 min, concentrated and purified by reverse phase HPLC (YMC-C18 column, mobile phase=45% to 100% MeCN/H$_2$O, both containing 0.1% TFA) to provide the title compounds. LCMS (ESI): m/z 502.3 [M+1]$^+$. $^1$H NMR (500 MHz, acetone-d$_6$): δ (ppm) 7.84 (m, 3H), 7.78 (m, 2H), 7.73 (d, J=8.5 Hz, 1H), 7.49 (d, J=8.2 Hz, 2H), 7.40 (dd, J=8.6, 1.6 Hz, 1H), 7.24 (d, J=2.5 Hz, 1H), 7.40 (dd, J=8.9, 2.5 Hz, 1H), 4.27 (t, J=7.9 Hz, 1H), 4.10 (t, J=6.5

Hz, 2H), 3.62 (q, 2H), 2.63 (t, J=6.8 Hz, 2H), 2.46 (m, 2H), 2.20 (m, 2H), 1.81 (m, 2H), 1.53 (m, 2H), 0.98 (t, J=7.4 Hz, 3H).

EXAMPLE 5

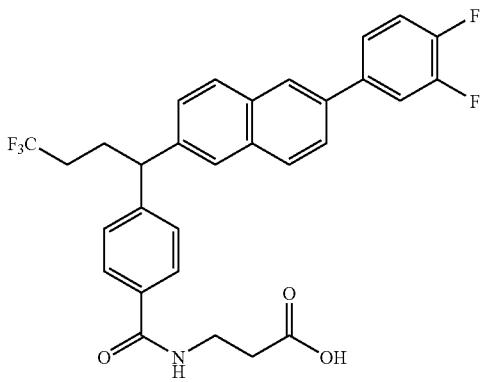

Step A: tert-Butyl-N-{4-[(1R or S)-4,4,4-trifluoro-1-(6-{[(trifluoromethyl)sulfonyl]oxy}-2-naphthyl)butyl]benzoyl}-β-alaninate To a cold (−78° C.) anhydrous solution of Enantiomer B from Example 4, Step D (500 mg, 1.0 mmol) in $CH_2Cl_2$ (10 mL) were added pyridine (0.21 mL, 2.60 mmol), and trifluoromethanesulfonic anhydride (0.20 mL, 1.2 mmol) under a nitrogen atmosphere. The dry ice/acetone bath was removed and the mixture was allowed to stir for 10 min. The solution was cooled to −78° C. and the reaction was quenched with EtOAc/hexanes (2:1 v/v), and water. The organic phase was collected and passed through a short silica plug. The filtrate was concentrated in vacuo to give the title compound as a foamy solid. LCMS (ESI): m/z 656.2 [M+Na]$^+$.

Step B: N-{4-[(1R or S)-4,4,4-Trifluoro-1-(6-{[(trifluoromethyl)sulfonyl]oxy}-2-naphthyl)butyl]benzoyl}-β-alanine To an anhydrous solution of the title compound from the previous reaction (5 mg, 0.008 mmol) in DME (0.3 mL) in a 4 mL vial were added 3,4-difluorophenylboronic acid (2-5 mg, 0.016 mmol), Pd(PPh$_3$)$_4$ (1.2 mg, 0.0010 mmol), and triethylamine (0.006 mL, 0.043 mmol). The vial was purged with N$_2$ and sealed, then stirred at 125° C. for 15 min. After cooling to room temperature, the mixture was concentrated under a stream of nitrogen. The residue was then dissolved in $CH_2Cl_2$ (0.2 mL) and TFA (0.2 mL). After 30 min the mixture was concentrated in vacuo. Purification by reverse phase HPLC (30% to 100% $CH_3CN/H_2O$, each with 0.05% TFA) provided the title compound. LCMS (ESI): m/z 542.2 [M+H]$^+$. $^1$H NMR (500 MHz, Acetone-d$_6$) δ 8.18 (s, 1 H), 8.04-7.93 (m, 3 H), 7.87 (d, J=8.2 Hz, 2 H), 7.81-7.74 (m, 1 H), 7.68-7.62 (m, 1 H), 7.54 (d, J=8.2 Hz, 2 H), 7.50-7.42 (m, 1 H), 4.37 (t, J=8.0 Hz, 1 H), 3.68 (quart, J=6.6 Hz, 2 H), 2.64 (t, J=6.8 Hz, 2 H), 2.58-2.44 (m, 2 H), 2.31-2.17 (m, 2 H).

EXAMPLE 6

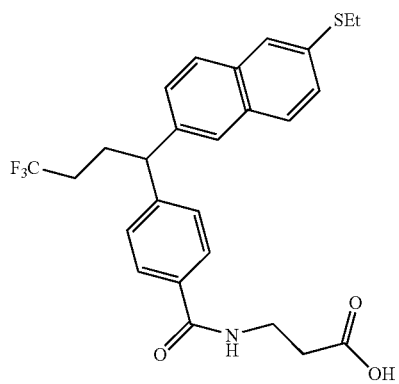

Step A: N-(4-{(1R or S)-1-[6-(Ethylthio)-2-naphthyl]-4,4,4-trifluorobutyl}benzoyl)-β-alanine A solution of title compound of Example 5, Step A (10 mg, 0.016 mmol), Pd$_2$dba$_3$ (1.5 mg, 0.0016 mmol), Xantphos (1.8 mg, 0.003 mmol), DIEA (12 mg, 0.09 mmol) and ethanethiol (4 mg, 0.07 mmol) in 0.3 mL of 1,4-dioxane was heated in a sealed vial for 1 h at 120° C. The reaction mixture was purified by preparative TLC on silica eluting with 3:2 (v/v) hexanes:EtOAc. A portion of the thioether thus obtained was treated with 1:1 (v/v) TFA:dichloromethane for 30 min. The crude material was concentrated and purified by reverse phase HPLC (YMC-C18 column, 45% to 100% MeCN/H$_2$O, both containing 0.05% TFA) to yield the title compound. LCMS (ESI): m/z 490.1 [M+1]$^+$. $^1$H NMR (500 MHz acetone-d$_6$): δ (ppm) 7.90 (s, 1H), 7.85 (m, 3H), 7.79 (m, 3H), 7.52 (d, J=8.0 Hz, 2H), 7.47 (m, 4H), 4.33 (t, J=7.9 Hz, 1H), 3.63 (q, 2H), 3.09 (q, 2H), 2.64 (t, J=6.9 Hz, 2H), 2.49 (m, 2H), 2.23 (m, 2H), 1.33 (t, J=7.3 Hz, 3H).

EXAMPLE 7

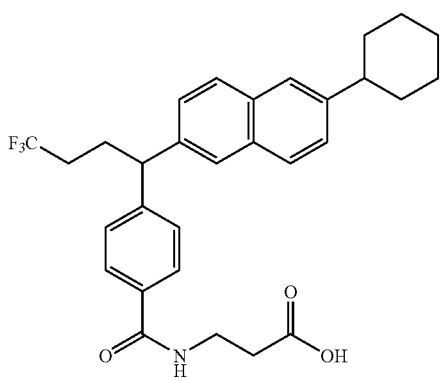

Step A: N-{4-[(1R or S)-1-(6-Cyclohexyl-2-naphthyl)-4,4,4-trifluorobutyl]benzoyl}-β-alanine To an anhydrous DME (0.3 mL) solution of the title compound from Example 5, Step A (5 mg, 0.0079 mmol) in a 4 mL vial were added cyclohexen-1-ylboronic acid (2.6 mg, 0.020 mmol), Pd(PPh₃)₄ (1.2 mg, 0.0010 mmol), and triethylamine (0.006 mL, 0.043 mmol). The vial was purged with N₂ and capped, then stirred at 125° C. for 15 min. The reaction mixture was allowed to cool and concentrated under a stream of N₂. The mixture was purified by preparative TLC on silica eluting with 2:1 (v/v) hexanes:EtOAc. The isolated product was dissolved in a solution of EtOAc (1 mL) and EtOH (0.2 mL), and then Pd black (1 mg) was added. The mixture was degassed and then stirred under H₂ (balloon) at rt for 2 h. The mixture was filtered through a short pad of silica gel and concentrated in vacuo. The residue was dissolved in CH₂Cl₂ (0.2 mL) and TFA (0.2 mL) was added. After 30 min, the mixture was concentrated in vacuo. Purification by reverse phase HPLC (55% to 100% CH₃CN in H₂O, each with 0.05% TFA) provided the title compound. LCMS (ESI): m/z 512.3 [M+H]⁺. ¹H NMR (500 MHz, Acetone-d₆): δ 7.92-7.73 (m, 5 H), 7.66 (s, 1 H), 7.51 (d, J=8.5 Hz, 2 H), 7.44 (d, J=8.5 Hz, 2H), 4.32 (t, J=8.0 Hz, 1 H), 3.63 (quart, J=6.6 Hz, 2 H), 2.64 (t, J=6.8 Hz, 2 H), 2.56-2.41 (m, 2 H), 2.28-2.16 (m, 2 H), 1.96-1.73 (m, 5 H), 1.64-1.27 (m, 6 H).

EXAMPLE 8

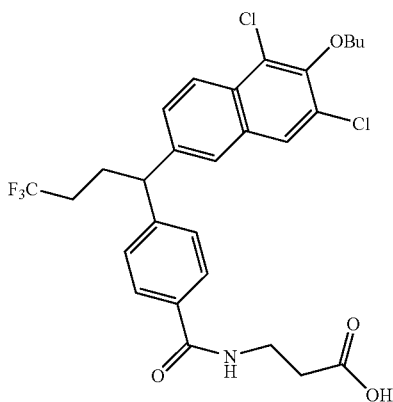

Step A: tert-Butyl N-{4-[(1R or S)-1-(6-butoxy-5,7-dichloro-2-naphthyl)-4,4,4-trifluorobutyl]benzoyl}-β-alaninate Enantiomer B of Example 4, Step D (I 00 mg) was treated with SO₂Cl₂ (0.35 mL) in 2 mL of CH₂Cl₂ for 7 h at rt. The reaction mixture was concentrated, stirred in a mixture of aq sodium hydrogensulfite and acetonitrile for 45 min, and purified by reverse phase HPLC (YMC-C18 column, 45% to 100% MeCN/H₂O, both containing 0.05% of TFA) to yield the title compound. LC-MS (ESI): m/z 514.1 [M+1]⁺.

Step B: N-{4-[(1R or S)-1-(6-Butoxy-5,7-dichloro-2-naphthyl)-4,4,4-trifluorobutyl]benzoyl}-β-alanine The title compound of the previous reaction (5 mg, 0.01 mmol) was stirred with cesium carbonate (8 mg, 0.025 mmol) in 0.1 mL of DMF containing 14% (v/v) of 1-iodobutane for 1 h. The reaction was repeated on a 3-fold larger scale for 2 h. The material from two reactions was combined, concentrated, and treated with a mixture of 0.15 mL of 1,4-dioxane, 0.15 mL of MeOH and 0.1 mL of 3 N NaOH (aq) at 50° C. for 30 min. The crude material was concentrated and purified by reverse phase HPLC (YMC-C18 column, 45% to 100% MeCN/H₂O, both containing 0.05% TFA) to yield the title compound. LCMS (ESI): m/z 570.1 [M+1]⁺. ¹H NMR (500 MHz, acetone-d₆): δ (ppm) 8.14 (d, J=8.9 Hz, 1H), 8.07 (s, 1H), 8.00 (s, 1H), 7.87 (d, J=8.2 Hz, 2H), 7.82 (t, 1H), 7.67 (dd, J=8.7, 1.6 Hz, 1H), 7.52 (d, J=8.2 Hz, 2H), 4.39 (t, J=8.0 Hz, 1H), 4.14 (t, J=6.4 Hz, 2H), 3.63 (m, 2H), 2.64 (t, J=6.9 Hz, 2H), 2.51 (m, 2H), 2.24 (m, 2H), 1.89 (m, 2H), 1.63 (m, 2H), 1.03 (t, J=7.4 Hz, 3H).

EXAMPLE 9

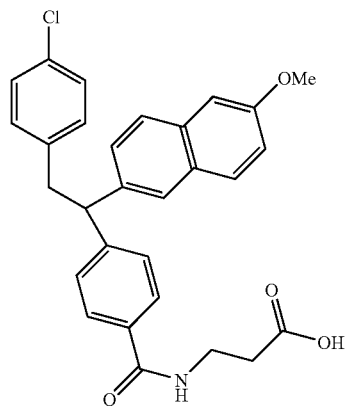

Step A: Methyl 4-[(6-methoxy-2-naphthyl)methyl]benzoate

The title compound of Example 1, Step A (0.97 g, 3 mmol) was treated with 50 mL of chloroform containing 3% each of TFA and triethylsilane for 2 h. The reaction was partitioned between aq sodium bicarbonate and EtOAc. The organic phase was concentrated and the resultant residue was purified by flash chromatography on silica gel (mobile phase=15:85 (v/v) EtOAc:hexanes) to provide the title compound.
¹H NMR (500 MHz, CDCl₃): δ (ppm) 7.98 (d, J=8.2 Hz, 2H), 7.69 (d, J=8.7 Hz, 2H), 7.57 (s, 1H), 7.31 (d, J=8.2 Hz, 2H), 7.27 (dd, J=8.5, 1.8 Hz, 1H), 7.14 (m, 2H), 4.18 (s, 2H), 3.93 (s, 3H), 3.92 (s, 3H).

Step B: Methyl 4-[(1RS)-2-(4-chlorophenyl)-1-(6-methoxy-2-naphthyl)ethyl]benzoate To a solution of the title compound from the previous reaction (100 mg, 0.33 mmol) and 4-chlorobenzyl bromide (335 mg, 1.63 mmol) in 2 mL of THF at 0° C. was added LHMDS (2.5 mL of a 1.0 M solution in THF, 2.5 mmol). The reaction mixture was allowed to stand at ambient temperature for 48 h. Aqueous workup (EtOAc/brine) followed by preparative TLC on silica gel (mobile phase=10% (v/v) EtOAc in hexanes) provided the title compound as a racemic mixture.
¹H NMR (500 MHz, CDCl₃): δ (ppm) 7.94 (d, J=8.0 Hz, 2H), 7.60 (s, 1H), 4.37 (t, J=7.8 Hz, 1H), 3.92 (s, 3H), 3.90 (s, 3H), 3.44 (m, 2H).

Step C: N-{4-[(1RS)-2-(4-Chlorophenyl)-1-(6-methoxy-2-naphthyl)ethyl]benzoyl}-β-alanine The title compound from the previous reaction (39 mg, 0.09 mmol) was stirred in a mixture of 1 mL of 1,4-dioxane and 0.5 mL of water containing LiOH (40 mg, 1.67 mmol) at 60° C. for 2.5 h. The reaction mixture was acidified with 1 N HCl and extracted with EtOAc. The organic phase was concentrated and the crude carboxylic acid was taken up in 0.5 mL of DMF and treated with β-alanine tert-butyl ester hydrochloride (19 mg, 0.10 mmol), HOBt (16 mg, 0.12 mmol), EDC (20 mg, 0.10 mmol) and DIEA (0.026 mL, 0.15 mmol). The reaction mixture was heated for 1 h 15 min at 45° C. and partitioned between water and hexanes-EtOAc. The organic phase was concentrated and the residue was treated with 1 mL of dichloromethane and 0.5 mL of TFA for 2 h. The crude material was concentrated and purified by preparative TLC on silica gel (mobile phase=6% MeOH in dichloromethane) to provide the title compound as a racemic mixture. LC-MS (ESI): m/z 460.2 [M+1]$^+$. $^1$H NMR (500 MHz, CD$_2$Cl$_2$): δ (ppm) 7.64 (m, 4H), 7.57 (s, 1H), 7.25 (br m, 4H), 7.11 (m, 4H), 6.97 (d, 2H), 4.34 (t, 1H), 3.86 (s, 3H), 3.39 (m, 2H).

EXAMPLE 10

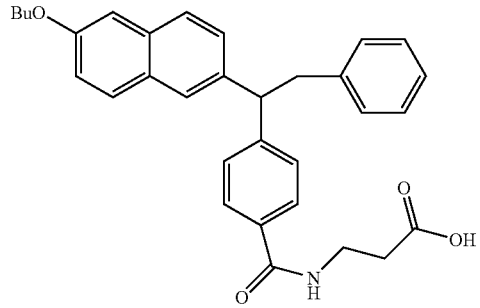

Step A: Benzyl 4-[(RS)-hydroxy(6-methoxy-2-naphthyl)methyl]benzoate n-BuLi (15 mL of a 2.0 M solution in cyclohexane, 30 mmol) was added dropwise to a solution of 6-methoxy-2-bromonaphthalene (5.9 g, 25 mmol) in 200 mL of dry THF cooled in dry ice-acetone bath. After 15 min, 4-benzyloxybenzaldehyde (5.3 g, 25 mmol) was added. After stirring for an additional 30 min, the cold bath was allowed to slowly warm to −60° C. over 30 min. The reaction vessel was removed from the cold bath for 10 min, then cooled to −78° C. The reaction mixture was quenched with aq ammonium chloride, diluted with hexanes and allowed to stand at 4° C. for 48 h. Chloroform was added to dissolve the precipitate. The mixture was dried with sodium sulfate and concentrated to about 100 mL, upon which a precipitate formed. Hexanes (100 mL) was added and the solid was filtered and washed with a mixture of 100 mL of hexanes and 50 mL of EtOAc to provide the title compound as a racemic mixture. LCMS (ESI): m/z 353.1 [M−OH]$^+$. $^1$H NMR (500 MHz, CD$_2$Cl$_2$): δ (ppm) 7.82 (s, 1H), 7.74 (m, 2H), 7.46-7.32 (m, 8H), 7.16 (m, 2H), 6.96 (d, J=8.7 Hz, 2H), 5.94 (d, J=2.3 Hz, 1H), 5.07 (s, 2H), 3.92 (s, 3H).

Step B: Benzyl 4-(6-methoxy-2-naphthoyl)benzoate

To the title compound from the previous reaction (2.45 g, 6.62 mmol) in 120 mL of dry dichloromethane at 0° C. was added successively 4-methylmorpholine N-oxide (930 mg, 7.3 mmol), 4A powdered molecular sieves (3.6 g) and tetrapropylammonium perruthenate (232 mg, 0.66 mmol). After 30 min the reaction was passed through a pad of celite. The filtrate was concentrated and purified by flash chromatography on silica gel (mobile phase=1:5 (v/v) EtOAc in hexanes) to give the title compound. LCMS (EST): m/z 369.1 [M+H]$^+$. $^1$H NMR (500 MHz, CD$_2$Cl$_2$): δ (ppm) 8.21 (s, 1H), 7.25 (m, 2H), 7.12 (d, J=8.9 Hz, 2H), 5.21 (d, J=2.3 Hz, 1H), 3.99 (s, 3H).

Step C: Butyl 4-[(1RS)-1-(6-methoxy-2-naphthyl)-2-phenylethyl]benzoate

The title compound from the previous reaction (300 mg, 0.82 mmol) in 4 mL of THF and benzyl magnesium chloride (0.82 mL of a 2.0 M solution in THF, 1.6 mmol) were reacted at 4° C. for 16 h. The mixture was quenched with aq ammonium chloride, acidified with dilute HCl and extracted with hexanes-EtOAc. The organic layer was concentrated and the crude material was taken up in 2.4 mL of dichloromethane and treated with 0.4 mL of triethylsilane and 0.25 mL of TFA for 30 min. The crude reaction mixture was concentrated twice from toluene and once from EtOAc. The residue was suspended in 3 mL of 1:1 (v/v) EtOH:EtOAc, and stirred with 100 mg of 10% Pd/C under H$_2$ (balloon) for 16 h. AcOH (0.25 mL) was added and the reaction was stirred under H$_2$ for additional 8 h. The reaction mixture was filtered and the filtrate was concentrated in vacuo. The resulting residue was taken up in dichloromethane (3 mL) and treated with pyridine (0.15 mL, 1.8 mmol) and trifluoromethanesulfonic anhydride (0.15 mL, 0.9 mmol). The reaction mixture was partitioned between 1 N HCl/hexanes-EtOAc. The aqueous layer was washed with dichloromethane and the combined organic phase was dried over sodium sulfate, passed through a plug of silica gel and concentrated. The residue was taken up in 4 mL of butanol and 60 mg of PdCl$_2$(dppf)$_2$, dichloromethane adduct (60 mg, 0.08 mmol) and DIEA (0.18 mL, 1 mmol) were added. The reaction was stirred at 90° C. under CO (balloon) for 35 min and the reaction was concentrated in vacuo. Flash chromatography on silica gel eluting with 9:1 (v/v) hexanes:EtOAc gave the title compound as a racemic mixture.

$^1$H NMR (500 MHz, CD$_2$Cl$_2$): δ (ppm) 7.93 (d, J=8.2 Hz, 2H), 7.36 (d, J=8.2 Hz, 2H), 7.34 (dd, J=8.5, 1.8 Hz, 1H), 4.50 (t, J=7.9 Hz, 1H), 4.29 (t, J=6.5 Hz, 2H), 3.92 (s, 3H), 3.52 (m, 2H), 1.74 (m, 2H), 1.48 (m, 2H), 0.98 (t, J=7.4 Hz, 3H).

Step D: N-{4-[1(RS)-1-(6-Butoxy-2-naphthyl)-2-phenylethyl]benzoyl}-β-alanine The title compound from the previous step was processed using procedures described in Example 4, Steps D and E to provide the title compound as a racemic mixture. LC-MS (ESI): m/z 496.1 [M+1]$^+$. $^1$H NMR (500 MHz, acetone-d$_6$): δ (ppm) 4.58 (t, J=7.9 Hz, 1H), 4.10 (t, J=6.5 Hz, 2H), 3.61 (m, 2H), 3.53 (m, 2H), 2.63 (t, J=6.9 Hz, 2H), 1.81 (m, 2H), 1.53 (m, 2H), 1.00 (t, J=7.4 Hz, 3H).

EXAMPLE 11

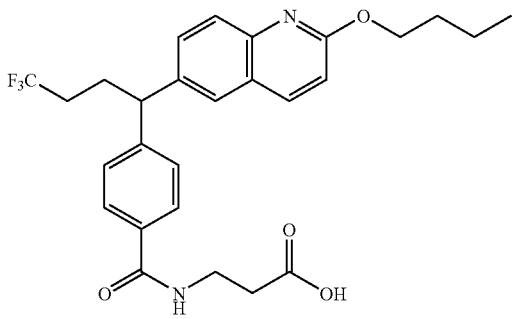

Step A: (1RS)-4,4,4-Trifluoro-1-(2-methoxyquinolin-6-yl)butan-1-ol

To a cold (−78° C.) anhydrous solution of 6-bromo-2-methoxyquinoline (3.95 g, 16.7 mmol) in THF (60 mL) was added n-BuLi (9.0 mL of a 2.5 M solution in hexanes, 23 mmol). The mixture was stirred at −78° C. under nitrogen for 15 min, then 4,4,4-trifluorobutylaldehyde (1.75 g, 13.9 mmol) was added slowly to the reaction mixture. The bath was allowed to warm to room temperature and the reaction mixture was quenched with saturated NH$_4$Cl (aq). The resultant mixture was extracted with EtOAc/hexanes. The organic layer was evaporated in vacuo and the crude residue was purified by flash chromatography on silica gel, eluting with a gradient of 0% to 65% EtOAc/hexanes to provide to provide the title compound as a racemic mixture. LCMS: m/z=286.2 [M+H]$^+$. $^1$H NMR (500 MHz, CDCl$_3$): δ 8.01 (d, J=8.7, 1 H), 7.92 (d, J=8.7, 1 H), 7.71 (s, 1 H), 7.64 (dd, J=8.5, 1.8, 1 H), 6.69 (d, J=8.9 Hz, 1 H), 4.97-4.92 (m, 1H), 2.37-2.04 (m, 4 H).

Step B: 4-[1(RS)-4,4,4-Trifluoro-1-(2-methoxyquinolin-6-yl)butyl]phenol

To phenol (1.4 g, 15 mmol) dissolved in trifluoromethanesulfonic acid (0.44 mL, 5 mmol) was added the title compound from the previous reaction (2.9 g, 10 mmol). The mixture was stirred at room temperature overnight, cooled in an ice-water bath and quenched by slow addition of saturated aqueous NaHCO$_3$. The resulting mixture was extracted with EtOAc. The organic layer was concentrated in vacuo and the crude residue was purified by flash chromatography on silica gel using gradient elution (0% to 35% EtOAc/hexanes, 500 mL; 35% to 75% EtOAc/hexanes, 2000 mL) to provide the title compound as a racemic mixture. LCMS, m/z 362.3 [M+H]$^+$. $^1$H NMR (500 MHz, CD$_2$Cl$_2$): δ 7.98 (d, J=8.9 Hz, 1 H), 7.76 (d, J=8.7 Hz, 1 H), 7.61 (d, J=2.1 Hz, 1 H), 7.49 (dd, J=8.7, 2.1 Hz, 1 H), 7.16 (d, J=6.3 Hz, 2 H), 6.91 (d, J=8.9 Hz, 1 H), 6.80 (d, J=8.5, 2H), 4.51-4.41 (m, 1 H). 4.05 (s, 3 H), 2.43-2.30 (m, 2 H), 2.16-2.04 (m, 2 H).

Step C: Butyl 4-[(1RS)-4,4,4-trifluoro-1-(2-methoxyquinolin-6-yl)butyl]benzoate

To a solution of the title compound from the previous reaction (2.0 g, 5.5 mmol) in anhydrous CH$_2$Cl$_2$ (30 mL) were added pyridine (0.67 mL, 8.3 mmol) followed by trifluoromethansulfonic anhydride (1.1 mL, 6.6 mmol). The mixture was stirred at room temperature for 20 min, quenched with water and extracted with EtOAc/hexanes. The organic phase was washed twice with H$_2$O and once with brine, dried over Na$_2$SO$_4$ and passed through a short silica plug. The filtrate was concentrated to dryness to provide the triflate as a solid. The triflate thus obtained was taken up in n-butanol (50 mL), then dichloro[1,1'-bis(diphenylphosphino)ferrocene] palladium(II), dichloromethane adduct (476 mg, 0.65 mmol) and DIEA (2.85 mL, 16.2 mmol) were added. The reaction mixture was stirred at 95° C. under a CO atmosphere (balloon) for 2 h. The resulting mixture was concentrated and purified by flash chromatography on silica gel using gradient elution (0% to 25% EtOAc/hexanes, 450 mL; 25% to 70% EtOAc/hexanes, 2049 mL) to provide the title compound as a racemic mixture. LCMS (ESI): m/z=446.4 [M+H]$^+$. $^1$H NMR (500 MHz, CD$_2$Cl$_2$) δ 8.02-7.97 (m, 3 H), 7.78 (d, J=8.7 Hz, 1 H), 7.64 (d, J=1.8 Hz, 1 H), 7.50 (dd, J=8.7, 2.1 Hz, 1 H), 7.40 (d, J=8.5 Hz, 2 H), 6.93 (d, J=8.7 Hz, 1 H), 4.30 (t, J=6.6 Hz, 2 H), 4.18 (t, J=8.0 Hz, 1 H), 4.05 (s, 3H), 2.51-2.38 (m, 2 H), 2.19-2.04 (m, 2 H), 1.80-1.68 (m, 2 H), 1.53-1.42 (m, 2H), 0.99 (t, J=7.3 Hz, 3 H).

Step D: tert-Butyl N-{4-[(1R)-4,4,4-trifluoro-1-(2-hydroxyquinolin-6-yl)butyl]benzoyl}β-alaninate and tert-Butyl N-{4-[(1S)-4,4,4-trifluoro-1-(2-hydroxyquinolin-6-yl)butyl]benzoyl}-β-alaninate To a stirring solution of the title compound from the previous step (1.6 g, 3.6 mmol) in anhydrous dichloroethane (16 mL) was slowly added trimethylsilyl iodide (2.7 mL, 18.7 mmol). The mixture was stirred at 65° C. for 3 h and concentrated in vacuo. The residue was reconcentrated first from toluene (60 mL), then from a mixture of 2-propanol (20 mL) and toluene (30 mL) to provide the crude phenol: LC-MS (ESI): m/z=432.2 [M+1]$^+$. The crude product was dissolved in 16 mL of a 1:1 mixture of 1,4-dioxane:MeOH, and NaOH (8 mL of a 3N solution, 24 mmol) was added. The mixture was stirred at 60° C. for 1.5 h. The mixture was allowed to cool to room temperature and acidified with 1 N aq HCl (35 mL). The aqueous phase was extracted with EtOAc and the organic phase was washed with brine, dried over anhydrous Na$_2$SO$_4$ and concentrated in vacuo to provide the crude carboxylic acid: LC/MS (ESI): m/z 376.2 [M+H]$^+$.

To the carboxylic acid obtained above were added EDC (1.0 g, 5.4 mmol), HOBt (0.73 g, 5.4 mmol) and β-alanine tert-butyl ester hydrochloride (0.98 g, 5.4 mmol). The combined solids were dissolved in DMF (20 mL), DIEA (2.4 mL, 13.5 mmol) was added, and the reaction mixture was stirred at 50° C. for 1 h. The reaction mixture was quenched by addition of water and the aqueous phase was extracted with EtOAc/hexanes. The organic phase was washed with water and brine, dried over Na$_2$SO$_4$ and concentrated in vacuo. The crude residue was purified by flash chromatography on silica gel using gradient elution (2% to 55% MeOH/dichloromethane) to give the racemic product as a light brown solid. LCMS (ESI): m/z 503.3 [M+H]$^+$.

The product enantiomers were resolved by chiral chromatography on a Chiralpak AD column eluting with 60:40 (v/v) isopropanol:heptane to provide Enantiomer A as the faster eluting product and Enantiomer B as the slower eluting product.

$^1$H NMR (500 MHz, CD$_2$Cl$_2$): δ 11.13 (s, 1 H) 7.78 (d, J=9.4 Hz, 1 H), 7.72 (d, J=8.2 Hz, 2 H), 7.46 (d, J=1.8 Hz, 1 H), 7.39 (dd, J=8.5, 2.1 Hz, 1 H), 7.35 (d, J=8.2 Hz, 2H), 7.27 (d, J=8.5 Hz, 1 H), 6.79 (t, J=6.0 Hz, 1H), 6.65 (d, J=9.6 Hz,

1 H), 4.08 (t, J=8.0 Hz, 1 H), 3.64 (quart, J=6.2 Hz, 2 H), 2.53 (t, J=6.2 Hz, 2 H), 2.38 (quart, J=8.0 Hz, 2 H), 2.15-2.03 (m, 2 H), 1.45 (s, 9 H).

Step E: N-{4-[(1R or S)-1-(2-Butoxyquinolin-6-yl)-4,4,4-trifluorobutyl]benzoyl}-β-alanine To an anhydrous DMF (0.15 mL) solution of Enantiomer B from the previous reaction (10 mg, 0.02 mmol) in a 4 mL vial was added Cs₂CO₃ (10 mg, 0.027 mmol). The mixture was stirred at rt for 10 min, then 1-iodobutane (0.010 mL, 0.102 mmol) was added. The mixture was stirred at 40° C. for 1 hour and concentrated in vacuo. The residue was dissolved in CH₂Cl₂ (0.2 mL) and TFA (0.2 mL) was added. After 30 min, the mixture was concentrated in vacuo. Purification by reverse phase HPLC (45% to 100% CH₃CN in H₂O, each with 0.05% v/v TFA) provided the title compound: LCMS (ESI): m/z 503.3 [M+H]⁺; ¹H NMR (500 MHz, d-Acetone): δ 8.15 (d, J=8.9 Hz, 1 H), 7.86 (d, J=8.2 Hz, 3 H), 7.81-7.76 (broad, 1 H), 7.73 (d, J=8.7 Hz, 1 H), 7.62 (dd, J=8.7, 2.1 Hz, 1 H), 7.51 (d, J=8.2 Hz, 2 H), 6.94 (d, J=8.7 Hz, 1 H), 4.44 (t, J=6.6 Hz, 2 H), 4.32 (t, J=8.0 Hz, 1 H), 3.63 (quart, J=6.6 Hz, 2 H), 2.64 (t, J=6.6 Hz, 2 H), 2.53-2.41 (m, 2 H), 2.27-2.15 (m, 2 H), 1.83-1.75 (m, 2H), 1.55-1.47 (m, 2 H), 0.98 (t, J=7.3 Hz, 3 H).

EXAMPLE 12

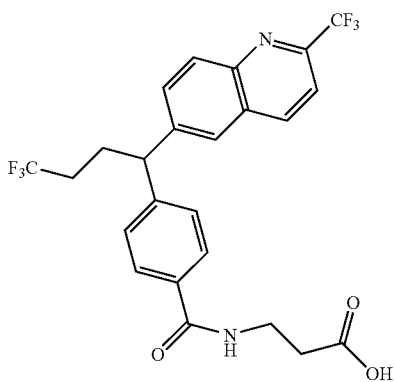

N-(4-{(1R or S)-4,4,4-Trifluoro-1-[2-(trifluoromethyl)quinolin-6-yl]butyl}benzoyl)-β-alanine To a cold (−78° C.) anhydrous solution of Enantiomer B from Example 11, Step D (266 mg, 0.53 mmol) in CH₂Cl₂ (6 mL) were added pyridine (0.112 ml, 1.38 mmol), and trifluoromethanesulfonic anhydride (0.11 mL, 0.64 mmol) under a nitrogen atmosphere. The dry ice-acetone bath was removed and the mixture was allowed to stir for 10 min. The solution was cooled to −78° C. and the reaction was quenched with EtOAc/Hexanes (2:1 v/v), and water. The organic phase was collected and passed through a short silica plug. The filtrate was concentrated in vacuo to give the triflate as a solid: LCMS (ESI): m/z 635.1 [M+H]⁺. A portion of this material (20 mg, 0.03 mmol), hexamethylditin (22 mg, 0.06 mmol), LiCl (14 mg, 0.3 mmol), and tetrakis(triphenylphosphine)palladium (0) (3.5 mg, 0.003 mmol) were heated in 0.5 mL of 1,4-dioxane in a capped vial at 125° C. for 15 min. The reaction mixture was cooled and concentrated in vacuo. The residue was dissolved in 0.5 mL of dichloromethane and iodine (40 mg, 0.16 mmol) was added in two portions over 2 h. The reaction mixture was washed with aq KF and aq sodium bicarbonate and the aqueous portion was extracted with EtOAc and dichloromethane. The combined organic phase was dried over sodium sulfate and passed through a pad of silica gel to give the crude iodide. A portion of the iodide thus obtained (6 mg, 0.01 mmol) was combined with CuI (26 mg, 0.14 mmol) and methyl 2,2-difluoro-2-(fluorosulfonyl)acetate (25 mg, 0.13 mmol) in 0.1 mL DMF and the resulting solution was heated in a capped vial at 125° C. for 1 h 15 min. A second reaction was carried out with 15 mg of this material. The two crude reaction mixtures were combined and concentrated in vacuo. The residue was treated with 1:1 dichloromethane:TFA for 30 min, concentrated and purified by reverse phase HPLC (YMC-C18 column, 45% to 100% MeCN/H₂O, both containing 0.05% TFA) to provide the title compound. LCMS (ESI): m/z 499.0 [M+1]⁺.

¹H NMR (500 MHz, acetone-d₆): δ (ppm) 8.67 (d, J=8.5 Hz, 1H), 8.19 (d, J=1.8 Hz, 1H), 8.12 (d, J=8.9 Hz, 1H), 7.90 (m, 4H), 7.82 (t, 1H), 7.56 (d, J=8.2 Hz, 2H), 4.48 (t, J=8.0 Hz, 1H), 3.64 (q, 2H), 2.65 (t, J=6.9 Hz, 2H), 2.55 (m, 2H), 2.26 (m, 2H).

EXAMPLE 13

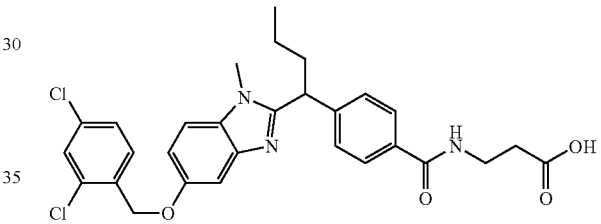

Step A. tert-Butyl (4-bromophenyl)acetate

To a solution of 4-bromophenylacetic acid (5.00 g, 23.2 mmol) in tBuOAc (75 mL) was added BF₃.OEt₂ (2.95 mL, 23.2 mmol). The mixture was allowed to stir overnight at room temperature and poured into H₂O. The aqueous phase was extracted with EtOAc. The organic phase was washed with sat. aq NaHCO₃, dried over anhydrous Na₂SO₄, and concentrated in vacuo. Purification by flash chromatography on silica gel (0% to 100% EtOAc in hexanes) provided the title compound. ¹H NMR (500 MHz, CDCl₃): δ 7.48 (d, J=8.0 Hz, 2 H), 7.19 (d, J=8.0 Hz, 2 H), 3.52 (s, 2 H), 1.48 (s, 9 H).

Step B. Butyl 4-(2-tert-butoxy-2-oxoethyl)benzoate

To an N₂-purged flask containing the title compound from the previous step (1.55 g, 5.55 mmol), were added PdCl₂(PPh₃)₂ (584 mg, 0.83 mmol), n-BuOH (30 mL), and DIEA (5.00 mL, 27.8 mmol). The mixture was placed under an atmosphere of carbon monoxide and stirred vigorously at 110° C. After 1 h, the reaction mixture was allowed to cool to room temperature, and was concentrated in vacuo. Purification by silica gel chromatography (0 to 100% EtOAc in hexanes) provided the title compound: LCMS (ESI): m/z 237.3 [M−tBu]⁺; ¹H NMR (500 MHz, CDCl₃): δ 7.99 (d, J=8.0 Hz, 2 H), 7.34 (d, J=8.0 Hz, 2 H), 4.32 (t, J=6.5 Hz, 2 H), 1.77-1.72 (m, 2 H), 1.51-1.45 (m, 2 H), 1.43 (s, 9 H), 0.98 (t, J=8.0 Hz, 3 H).

Step C. Butyl 4-{(1RS)-1-(tert-butoxycarbonyl)butyl]benzoate

To a solution of the title compound from the previous step (749 mg, 2.56 mmol) in DMF (8 mL) was added sodium hydride (113 mg of a 60% dispersion in mineral oil, 2.82 mmol). After 10 min, 1-iodopropane (0.275 mL, 2.82 mmol) was added, and the reaction mixture was stirred at 70° C. After 1 h, the mixture was quenched by the addition of $H_2O$. The aqueous phase was extracted with EtOAc, and the organic phase was concentrated in vacuo. Purification by silica gel chromatography (0% to 100% EtOAc in hexanes) provided the title compound as a racemic mixture. LCMS (ESI): m/z 279.1 [M−tBu]$^+$. $^1$H NMR (500 MHz, CDCl$_3$): δ 7.98 (d, J=7.5 Hz, 2 H), 7.36 (d, J=7.5 Hz, 2 H), 4.31 (t, J=6.5 Hz, 2 H), 3.50 (t, J=8.0 Hz, 1 H), 2.06-1.98 (m, 1 H), 1.77-1.66 (m, 4 H), 1.51-1.45 (m, 2 H), 1.44 (s, 9 H), 1.33-1.22 (m, 1 H), 0.98 (t, J=7.5 Hz, 3 H), 0.91 (t, J=7.5 Hz, 3 H).

Step D. Butyl 4-[(1RS)-1-(chlorocarbonyl)butyl]benzoate

To a solution of the title compound of the previous step (645 mg, 1.93 mmol) in CH$_2$Cl$_2$ (5 mL) was added TFA (2.5 mL). After 2 h, the reaction mixture was concentrated in vacuo. The crude carboxylic acid was dissolved in thionyl chloride (3 mL), and stirred at 80° C. After 2 h, reaction mixture was concentrated in vacuo and used without further purification.

Step E. Butyl 4-[(1RS)-1-(5-methoxy-1-methyl-1H-benzimidazol-2-yl)butyl]benzoate To a solution of the title compound of the previous step (1.9 mmol) in CH$_2$Cl$_2$ (5 mL) were added pyridine (0.625 mL, 7.72 mmol), followed by 4-methoxy-1-methylphenylene diamine (470 mg, 3.80 mmol). After 12 h, the reaction mixture was washed with 2 N HCl, and the organic phase was dried over anhydrous Na$_2$SO$_4$ and concentrated in vacuo. The crude amide was dissolved in POCl$_3$ (3 mL), and was stirred at 80° C. After 12 h, the reaction mixture was concentrated in vacuo, then redissolved in DCM, and washed with sat. aq NaHCO$_3$. The organic phase concentrated in vacuo. Purification by silica gel chromatography (0 to 100% EtOAc in hexanes) provided the title compound as a racemic mixture. LCMS (ESI): m/z 395.2 [M+1]$^+$.

Step F. Butyl 4-[(1RS)-1-(5-hydroxy-1-methyl-1H-benzimidazol-2-yl)butyl]benzoate To a cooled (−78° C.) solution of the title compound of the previous step (146 mg, 0.37 mmol) in CH$_2$Cl$_2$ (3 mL), was added BBr$_3$ (1.85 mL, 1.0 M in CH$_2$Cl$_2$, 1.85 mmol). The reaction mixture was then removed from the cooling bath and allowed to stir at room temperature. After 2 h, the reaction mixture was cooled to −78° C. and was quenched by addition of MeOH. The mixture was diluted with CH$_2$Cl$_2$, and the organic phase was washed with sat. aq NaHCO$_3$ and concentrated in vacuo. Purification by silica gel chromatography (0% to 100% EtOAc in hexanes) provided the title compound as a racemic mixture. LCMS (ESI): m/z 381.2 [M+1]$^+$.

Step G. 3-{[4-((1RS)-1-[5-[(2,4-Dichlorobenzyl)oxy]-1-methyl-1H-benzimidazol-2-yl}butyl)benzoyl]amino}propanoic Acid To a solution of the title compound of the previous step (17 mg, 0.05 mmol) in DMF (1 mL), were added Cs$_2$CO$_3$ (44 mg, 0.14 mmol) and 2,4-dichlorobenzyl chloride (0.010 mL, 0.07 mmol), and the resulting mixture was stirred at 45° C. After 2 h, the reaction mixture was quenched by addition of pH 7 buffer. The aqueous phase was extracted with EtOAc, and the organic phase was concentrated in vacuo: LCMS (ESI): m/z 539.2 [M+H]$^+$. To a solution of the crude adduct in 1,4-dioxane (1 mL) was added LiOH (0.5 mL, 2.0 M aqueous, 1.0 mmol), and the mixture was allowed to stir overnight at 40° C. The reaction mixture was quenched by addition of 2 N HCl and extracted with EtOAc. The organic phase was dried over anhydrous Na$_2$SO$_4$ and concentrated in vacuo: LCMS (ESI): m/z 483.1 [M+H]$^+$. To the crude carboxylic acid were added EDC (60.0 mg, 0.31 mmol), HOBt (43 mg, 0.31 mmol), β-alanine ethyl ester hydrochloride (45 mg, 0.31 mmol). The mixture was dissolved in DMF (1 mL), followed by addition of DIEA (0.22 mL, 1.24 mmol), and the reaction mixture was stirred at 40° C. After 12 h, the reaction mixture was quenched by addition of brine and extracted with EtOAc. The organic phase was concentrated in vacuo: LCMS (ESI): m/z 582.2 [M+H]$^+$. The crude amide was then redissolved in 1,4-dioxane (2 mL). Lithium hydroxide (1 mL, 2 N aqueous, 2.0 mmol) was added, and the mixture was allowed to stir for 1 h, at which time it was neutralized with 2 N aqueous HCl and purified by reverse phase HPLC (20% to 100% CH$_3$CN in H$_2$O, each with 0.1% v/v TFA) to provide the title compound as a racemic mixture. LCMS (ESI): m/z 554.1 [M+1]$^+$. $^1$H NMR (500 MHz, d$_6$-DMSO): δ 8.48 (t, J=5.5 Hz, 1 H), 7.79 (d, J=7.0 Hz, 2 H), 7.71 (d, J=2.0 Hz, 1 H), 7.63 (d, J=8.0 Hz, 2 H), 7.48 (dd, J=8.0, 2.0 Hz, 1 H), 7.44 (d, J=8.0 Hz, 2 H), 7.28 (d, J=2.0 Hz, 1 H), 7.18-7.14 (m, 1 H), 5.23 (s, 2 H), 4.65 (br m, 1 H), 3.75 (s, 3 H), 2.35-2.22 (m, 1 H), 2.10-2.07 (m, 1 H), 1.32-1.23 (m, 2 H), 0.91 (t, J=7.0 Hz, 3 H).

EXAMPLE 14

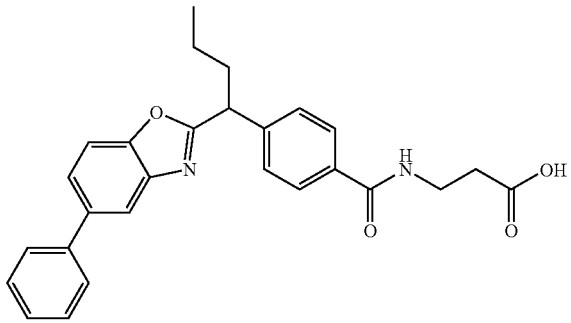

Step A. Butyl 4-[(1(RS)-1-(5-phenyl-1,3-benzoxazol-2-yl)pentyl]benzoate

To a solution of the title compound of Example 13, Step D (ca. 0.58 mmol) in dichloromethane (5 mL) were added pyridine (0.192 mL, 2.32 mmol), followed by 2-amino-4-phenylphenol (211 mg, 1.16 mmol), and the mixture was allowed to stir at ambient temperature. After 14 h, the reaction mixture was quenched by addition of saturated aqueous NaHCO$_3$, diluted with EtOAc, and the phases were separated. The organic phase was dried over anhydrous Na$_2$SO$_4$ and concentrated in vacuo, and taken forward without purification: LCMS (ESI): m/z 446.1 [M+H]$^+$. To a solution of the crude amide obtained above in THF (5 mL) were added triphenylphosphine (455 mg, 1.74 mmol) and DIAD (0.343 mL, 1.74 mmol), and the mixture was allowed to stir at ambient temperature. After 5 h, the mixture was concentrated in vacuo and purified by chromatography on silica gel (0% to 100% EtOAc in hexanes) to provide the benzoxazole ester as a racemic mixture. LCMS (ESI): m/z 428.3 [M+H]$^+$.

Step B. 3-({4-[(1(RS)-1-(5-Phenyl-1,3-benzoxazol-2-yl)butyl]benzoyl}amino)propanoic Acid To a solution of the title compound of the previous step (88 mg, 0.21 mmol) in 1,4-dioxane (2 mL) was added LiOH (0.5 mL, 2.0 M aqueous, 1.0 mmol), and the mixture was allowed to stir overnight at 40° C. The reaction mixture was quenched by addition of 2 N HCl and extracted with EtOAc. The organic phase was dried over anhydrous $Na_2SO_4$ and concentrated in vacuo. To the crude carboxylic acid were added EDC (118 mg, 0.62 mmol), HOBt (84 mg, 0.62 mmol), β-alanine ethyl ester hydrochloride (95 mg, 0.62 mmol). The mixture was dissolved in DM (1 mL), followed by addition of DIEA (0.22 mL, 1.24 mmol), and the reaction mixture was stirred at 40° C. After 12 h, the reaction mixture was quenched by addition of brine and extracted with EtOAc. The organic phase was concentrated in vacuo, then redissolved in 1,4-dioxane (2 mL). Lithium hydroxide (1 mL of 2 N aqueous, 2.0 mmol) was added, and the mixture was allowed to stir for 1 h, at which time it was neutralized with 2 N aqueous HCl, and purified by reverse phase HPLC (20% to 100% $CH_3CN$ in $H_2O$, each with 0.1% v/v TFA) to provide the title compound as a racemic mixture. LCMS (ESI): m/z 443.2 [M+H]$^+$. $^1$H NMR (500 MHz, $d_6$-DMSO): δ 8.49 (t, J=5.5 Hz, 1 H), 7.98 (d, J=1.5 Hz, 1 H), 7.88 (d, J=8.0 Hz, 2 H), 7.72-7.68 (m, 3 H), 7.62 (dd, J=8.5, 2.0 Hz, 1 H), 7.48-7.44 (m, 4 H), 7.38-7.35 (m, 2 H), 4.47 (t, J=8.5 Hz, 1 H), 3.43 (q, J=7.0 Hz, 2 H), 2.47 (q, obscured by DMSO signal, 2 H), 2.31-2.25 (m, 1 H), 2.06-1.99 (m, 1 H), 1.34-1.22 (m, 2 H), 0.91 (t, J=8.0 Hz, 3 H).

EXAMPLE 15

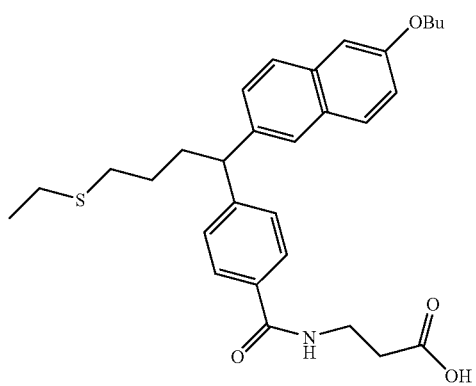

Step A: tert-Butyl N-{4-[(1R or S)-4-bromo-1-(6-butoxy-2-naphthyl)butyl]benzoyl}-β-alaninate Enantiomer B from Example 1, Step C (22 mg, 0.05 mmol) was stirred with cesium carbonate (28 mg, 0.09 mmol) in 0.5 mL DMF containing ca. 8% of 1-iodobutane overnight. The reaction mixture was partitioned between water and hexanes-EtOAc and the organic phase was dried over sodium sulfate and passed through a small plug of silica gel. The filtrate was concentrated, taken up in 0.3 mL of THF and treated with borane-THF (0.1 mL of a 1.0 M in THF, 0.1 mmol) for 30 min at 0° C. 3 N aq NaOH and 30% hydrogen peroxide were added. After stirring for 30 min, the crude mixture was treated with aq sodium hydrogensulfite for 5 min. The reaction was partitioned between water and EtOAc. The organic phase was concentrated and the residue was purified by reverse phase HPLC (YMC-C18 column, 45% to 100% MeCN/$H_2O$, both containing 0.05% TFA) to yield a solid. 5 mg of this material was treated with triphenylphosphine (5 mg, 0.02 mmol), carbon tetrabromide (5 mg, 0.015 mmol) and DIEA (0.014 mL, 0.08 mmol) for 20 min. The total amount of triphenylphosphine and carbon tetrabromide was tripled and the reaction mixture was stirred for additional 30 min. Prep TLC on silica (2:1 (v/v) hexane:EtOAc) gave the title product.

$^1$H NMR (500 MHz, $CD_2Cl_2$): δ (ppm) 7.70 (m, 5H), 7.40 (d, J=8.2 Hz, 2H), 7.31 (d, J=8.5 Hz, 1H), 7.14 (m, 2H), 6.75 (t, 11H), 3.64 (q, 2H), 3.48 (t, J=6.6 Hz, 2H), 2.54 (t, J=6.1 Hz, 2H), 2.32 (m, 2H), 2.56 (m, 2H), 1.47 (s, 9H), 1.02 (t, J=7.5 Hz, 3H).

Step B: N-{4-[(1R or S)-1-(6-Butoxy-2-naphthyl)-4-(ethylthio)butyl]benzoyl}-β-alanine The title compound from the previous reaction was treated with 0.1 mL of DMF containing 3 drops of DIEA and 3 drops of ethanethiol dispensed from a syringe equipped with a 21 G needle. After 72 h, the crude material was concentrated and the residue was treated with 1:1 TFA/$CH_2Cl_2$. The solvent was removed and the residue was purified by reverse phase HPLC (YMC-C18 column, gradient: 45% to 100% MeCN/$H_2O$, both containing 0.1% TFA) to provide the title compound. LCMS (ESI): m/z 508.1 [M+H]$^+$. $^1$H NMR (500 MHz, acetone-$d_6$) δ (ppm) 7.82 (d, J=8.5 Hz, 2H), 7.78 (m, 3H), 7.71 (d, J=8.7 Hz, 1H), 7.46 (d, J=8.2 Hz, 2H), 7.39 (dd, J=8.5, 1.6 Hz, 1H), 7.24 (d, J=2.3 Hz, 1H), 7.13 (dd, J=8.9, 2.5 Hz, 1H), 4.21 (t, J=7.9 Hz, 1H), 4.10 (t, J=6.4 Hz, 2H), 3.62 (q, 2H), 2.62 (m, 4H), 2.46 (q, 2H), 2.31 (m, 2H), 1.81 (m, 2H), 1.56 (m, 4H), 1.17 (t, J=7.4 Hz, 3H), 0.98 (t, J=7.4 Hz, 3H).

EXAMPLE 16

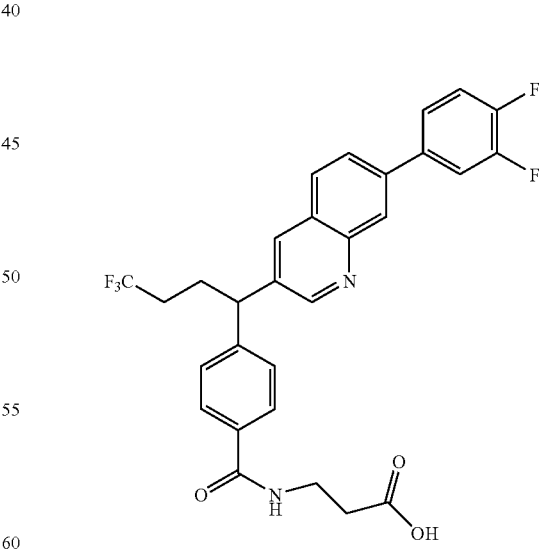

Step A: (1RS)-4,4,4-Trifluoro-1-(7-methoxyquinolin-3-yl)butan-1-ol

BuMgCl (0.16 mL of a 2 M solution in ether, 0.32 mmol) was added to 1 mL of toluene at −10° C. n-BuLi (0.26 mL of a 2.5 M solution in hexanes, 0.64 mmol) was added dropwise and the reaction mixture was allowed to age at −10° C. for 45 min. A solution of 3-bromo-7-methoxyquinoline (200 mg,) in 1 mL of toluene was added at −20° C. After 1 h, the reaction mixture was cooled to −78° C. and 4,4,4-trifluorobutyraldehyde (0.16 mL, 1 mmol) was added and the reaction mixture was slowly allowed to warm to ambient temperature. The procedure was repeated proportionally using 440 mg (1.8 mmol) of 3-bromo-7-methoxyquinoline. The two reactions were combined and partitioned between water and hexanes-EtOAc. The organic phase was concentrated and purified by flash chromatography on silica gel (25% to 66% EtOAc/hexanes) to provide the title compound as a racemic mixture. $^1$H NMR (500 MHz, CD$_2$Cl$_2$): δ (ppm) 8.71 (d, J=2.1 Hz, 1H), 8.06 (s, 1H), 7.70 (d, J=8.9 Hz, 1H), 7.35 (d, J=2.1 Hz, 1H), 7.21 (dd, J=8.9, 2.2 Hz, 1H), 4.93 (m, 1H), 3.93 (s, 3H), 2.33 (m, 2H).

Step B: 4-[(1-4,4,4-Trifluoro-1-(7-methoxyquinolin-3-yl)butyl]phenol

The title compound of the previous reaction (170 mg, 0.47 mmol) and phenol (210 mg, 2.2 mmol) were combined in 2 mL of trifluoromethanesulfonic acid for 2 h. The reaction mixture was partitioned between aq sodium bicarbonate and EtOAc. The organic phase was dried over sodium sulfate, concentrated in vacuo and purified by flash chromatography on silica gel (33% to 60% EtOAc/hexanes) to provide the title compound as a racemic mixture. LCMS (ESI): m/z 362.4 [M+H]$^+$. $^1$H NMR (500 MHz, CD$_2$Cl$_2$): δ (ppm) 8.69 (d, J=2.3 Hz, 1H), 7.96 (d, J=2.1 Hz, 1H), 7.73 (d, J=9.2 Hz, 1H), 7.40 (d, J=2.3 Hz, 1H), 7.23 (dd, J=9.2, 2.5 Hz, 1H), 7.16 (d, J=8.7 Hz, 2H), 6.81 (d, J=8.5 Hz, 2H), 4.08 (t, J=8.0 Hz, 1H), 3.96 (s, 3H), 2.40 (m, 2H), 2.14 (m, 2H).

Step C: Butyl 4-[(1RS)-4,4,4-trifluoro-1-(7-methoxyquinolin-3-yl)butyl]benzoate The title compound of the previous reaction (134 mg, 0.37 mmol) was converted to the butyl ester using procedures outlined in Example 11, Step C. LCMS (ESI): m/z 446.3 [M+1]$^+$.

Step D: Butyl 4-[(1RS)-4,4,4-trifluoro-1-(7-hydroxyquinolin-3-yl)butyl]benzoate The title compound of the previous reaction (87 mg, 0.24 mmol) was heated in neat pyridinium hydrochloride (120 mg) at 190° C. for 40 min and 170° C. for 16 h. Aqueous workup (water/EtOAc) provided the crude hydroxyquinoline as a racemic mixture which was used without further purification. LCMS (ESI): m/z 432.2 [M+1]$^+$.

Step E: tert-Butyl-N-{4-[(1R)-4,4,4-trifluoro-1-(7-hydroxyquinolin-3-yl)butyl]benzoyl}-β-alaninate and tert-Butyl-N-{4-[(1S)-4,4,4-trifluoro-1-(7-hydroxyquinolin-3-yl)butyl]benzoyl}-β-alaninate The title compound of the previous reaction was converted to the β-alanine tert-butyl ester using procedures described in Example 11, Step D. The product enantiomers were resolved by chiral chromatography on a Chiralpak AD column eluting with 60:40 (v/v) isopropanol:heptane to provide Enantiomer A as the faster eluting product and Enantiomer B as the slower eluting product. LCMS (ESI): m/z 503.3 [M+1]$^+$.

Step F: N-(4-{(1R)-1-[7-(3,4-Difluorophenyl)quinolin-3-yl]-4,4,4-trifluorobutyl}benzoyl)-β-alanine and N-(4-{(1S)-1-[7-(3,4-Difluorophenyl)quinolin-3-yl]-4,4,4-trifluorobutyl}benzoyl)-β-alanine Enantiomers A and B from the previous step were each converted to the final products as described in Example 5, Steps A and B.

LCMS (ESI): m/z 543.3 [M+H]$^+$. $^1$H NMR (500 MHz, Acetone-d$_6$) δ 8.52 (s, 1H), 8.36 (s, 1H), 8.12 (d, J=8.5 Hz, 1 H), 7.99 (dd, J=8.5, 1.6 Hz, 1H), 7.91 (d, J=8.2 Hz, 2 H), 7.84 (m, 2 H), 4.54 (t, J=7.9 Hz, 1 H), 3.63 (q, 2 H), 2.63 (m, 4 H), 2.31 (m, 2 H).

TABLE 1

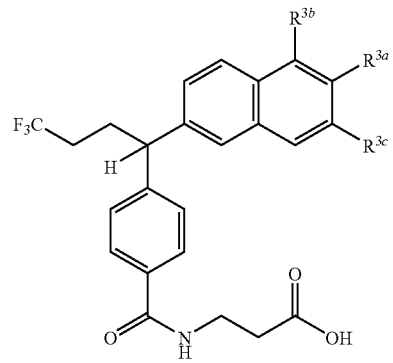

| Example | Enantiomer$^i$ | R$^{3a}$ | R$^{3b}$ | R$^{3c}$ | LCMS [M + 1]$^+$ |
|---|---|---|---|---|---|
| 17 | racemic | —OMe | H | H | 460.2 |
| 18 | racemic | 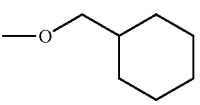 | H | H | 542.4 |

TABLE 1-continued

| Example | Enantiomer | $R^{3a}$ | $R^{3b}$ | $R^{3c}$ | LCMS [M + 1]⁺ |
|---|---|---|---|---|---|
| 19 | racemic | -OCH₂-(3-F-phenyl) | H | H | 554.2 |
| 20 | B | 3,4-dichlorophenyl | H | H | 574.1 |
| 21 | B | -pentyl | H | H | 500.2 |
| 22 | B | 3-fluorophenyl | H | H | 524.1 |
| 23 | B | 3-chloro-4-fluorophenyl | H | H | 558.1 |
| 24 | B | 3-(OCF₃)phenyl | H | H | 590.3 |
| 25 | B | 3-chloro-4-(CF₃)phenyl | H | H | 608.2 |
| 26 | B | 3,5-difluorophenyl | H | H | 542.1 |

TABLE 1-continued

[Structure: naphthalene with substituents R3a, R3b, R3c; attached via CH to F3C-CH2CH2 group and to a para-substituted benzamide linked to NH-CH2CH2-COOH]

| Example | Enantiomer[i] | R3a | R3b | R3c | LCMS [M + 1]+ |
|---|---|---|---|---|---|
| 27 | B | 4-Cl-3-CF3-phenyl | H | H | 608.2 |
| 28 | B | 3-Cl-phenyl | H | H | 540.2 |
| 29 | B | thiophen-3-yl | H | H | 512.2 |
| 30 | B | 4-F-3-Me-phenyl | H | H | 538.1 |
| 31 | B | 4-isopropyl-phenyl | H | H | 548.3 |
| 32 | B | 3,5-dichloro-phenyl | H | H | 574.1 |
| 33 | B | -hexyl | H | H | 514.3 |
| 34 | B | -heptyl | H | H | 528.3 |
| 35 | B | furan-3-yl | H | H | 496.2 |
| 36 | B | -CH2CH2-cyclohexyl | H | H | 540.3 |

TABLE 1-continued
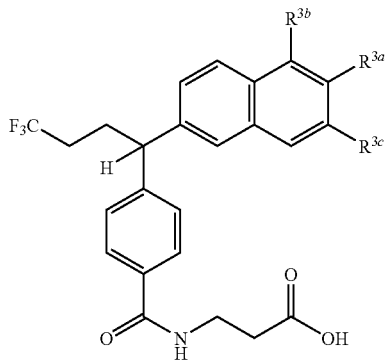
| Example | Enantiomer[i] | R³ᵃ | R³ᵇ | R³ᶜ | LCMS [M + 1]⁺ |
|---|---|---|---|---|---|
| 37 | B | cyclopentyl | H | H | 498.2 |
| 38 | B | CH₂CH₂C(CH₃)₃ | H | H | 514.3 |
| 39 | B | CH=CHC(CH₃)₃ | H | H | 512.3 |
| 40 | B | -Propyl | Cl | Cl | 540.2 |
| 41 | B | -Pentyl | Cl | Cl | 568.3 |
| 42 | B | cyclopentenyl | Cl | Cl | 564.3 |
| 43 | B | —SO₂Et | H | H | 522.1 |
| 44 | B | 2-EtO-5-CF₃-phenyl | H | H | 618.2 |
| 45 | B | —OBu | CN | Cl | 561.1 |
| 46 | B | —OCF₂H | CN | Cl | 555.1 |
| 47 | B | —OPr | CN | Cl | 547.2 |
| 48 | B | —OCH₂-cyclohexyl | CN | Cl | 601.2 |
| 49 | B | —SEt | CN | Cl | 549.1 |
| 50 | B | —SEt | —SEt | Cl | 575.1 |
[i]Enantiomer B derived from Enantiomer B from Example 4, Step D.

TABLE 2
| Example[ii] | R[1] | R[3a] | R[3b] | R[3c] | LCMS [M + 1]+ |
|---|---|---|---|---|---|
| 51[iii] | -allyl | —OButyl | H | H | 446.3 |
| 52 | -allyl | —OButyl | H | H | 446.3 |
| 53 | -hexyl | 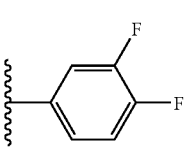 | H | H | 530.4 |
| 54 | 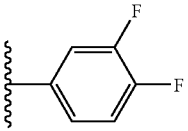 | 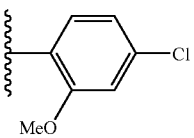 | H | H | 544.3 |
| 55 | -pentyl | 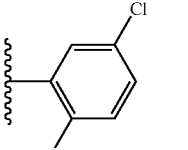 | H | H | 516.4 |
| 56 | -Butyl | 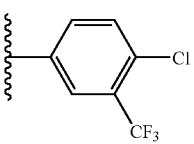 | H | H | 502.3 |
| 57[iv] | —Bn | —OMe | H | H | 454.1 |
| 58 | -Propyl | (3-Cl, 5-MeO-phenyl) | H | H | 516.2 |
| 59 | -Propyl | (5-Cl, 2-MeO-phenyl) | H | H | 516.2 |
| 60 | -Propyl | (4-Cl, 3-CF3-phenyl) | H | H | 554.2 |

TABLE 2-continued

| Example | R¹ | R³ᵃ | R³ᵇ | R³ᶜ | LCMS [M + 1]⁺ |
|---|---|---|---|---|---|
| 61 | -Propyl | 3-thienyl | H | H | 458.2 |
| 62 | -Propyl | cyclohexyl | H | H | 458.2 |
| 63 | -Propyl | 3-chlorophenyl | H | H | 486.1 |
| 64 | -Propyl | —SEt | H | H | 436.2 |
| 65 | -Propyl | —S-cyclopentyl | H | H | 476.2 |
| 66 | -Propyl | —S-isopropyl | H | H | 450.2 |
| 67 | -Propyl | 2-ethoxy-5-trifluoromethylphenyl | H | H | 564.3 |
| 68 | -Propyl | 2-chloropyridin-4-yl | H | H | 487.2 |
| 69 | -Propyl | 6-methoxypyridin-3-yl | H | H | 483.2 |
| 70 | -Propyl | 2-methoxypyrimidin-5-yl | H | H | 484.2 |
| 71 | -Propyl | —SPr | —CF₃ | H | 516.2 |
| 72 | -Propyl | —OBu | Cl | Cl | 516.1 |

TABLE 2-continued

| Example[ii] | R[1] | R[3a] | R[3b] | R[3c] | LCMS [M + 1]+ |
|---|---|---|---|---|---|
| 73 | -Propyl | —OBu | —SEt | H | 508.2 |
| 74 | -Propyl | —OBu | —Pr | H | 490.2 |
| 75 | -Propyl | 2-thienyl | H | H | 458.1 |
| 76 | -Propyl | 6-chloropyridin-3-yl | H | H | 487.1 |
| 77 | -Propyl | 3,5-dimethylisoxazol-4-yl | H | H | 471.2 |

[ii]All compounds derived from Enantiomer B from Example 1, Step C unless otherwise noted.
[iii]Compound derived from Enantiomer A from Example 1, Step C.
[iv]Compound is a racemic mixture

TABLE 3

| Example | Enantiomer[v] | R[3a] | R[3b] | LCMS [M + 1]+ |
|---|---|---|---|---|
| 78 | B | 3-fluorophenyl | H | 525.3 |
| 79 | B | -hexyl | H | 515.5 |
| 80 | B | 3,4-difluorophenyl | Cl | 577.1 |

TABLE 3-continued

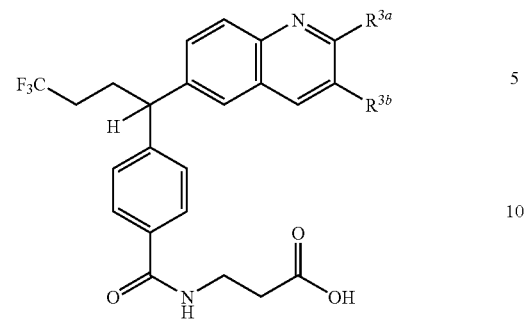

| Example | Enantiomer[v] | $R^{3a}$ | $R^{3b}$ | LCMS [M + 1]$^+$ |
|---|---|---|---|---|
| 81 | B | —OBu | Cl | 537.1 |
| 82 | B | —SEt | H | 491.1 |
| 83 | B | —SCF$_2$H | H | 513.1 |

[v]Compounds derived from Enantiomer B from Example 11, Step D.

TABLE 4

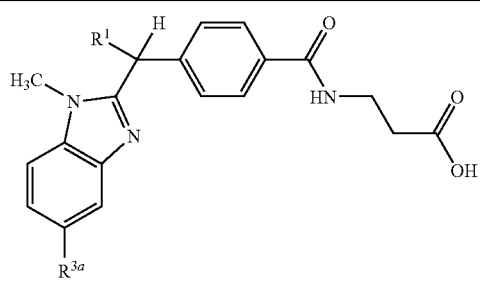

| Example | $R^1$ | $R^{3a}$ | Stereochemistry | LCMS [M + 1]$^+$ |
|---|---|---|---|---|
| 84 | (4-tert-butylbenzyl group) | Br | racemic | 562.1 |
| 85 | (2-cyclohexylethyl group) | OMe | racemic | 478.1 |
| 86 | n-hexyl | (cyclohexylmethoxy group) | racemic | 534.2 |
| 87 | n-hexyl | (2,4-dichlorobenzyloxy group) | racemic | 596.1 |
| 88 | (2-cyclohexylethyl group) | (cyclohexylmethoxy group) | racemic | 560.2 |

TABLE 4-continued

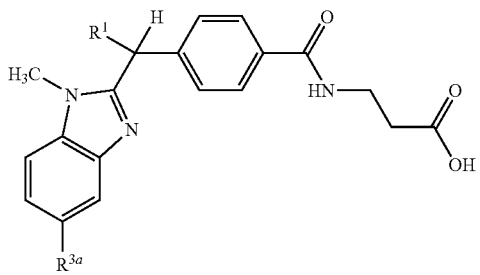

| Example | R¹ | R³ᵃ | Stereochemistry | LCMS [M + 1]⁺ |
|---|---|---|---|---|
| 89 | cyclohexylethyl | 2,4-dichlorobenzyloxy | racemic | 622.2 |
| 90 | cyclohexylethyl | 4-fluorobenzyloxy | racemic | 572.3 |

Biological Assays

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi et al. J Biol Chem 272, 7765-9 (1997); Cascieri et al. J Biol Chem 274, 8694-7 (1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl, 2 mM EDTA, 12% Glycerol, and 0.200 mg WGA coated PVT SPA beads (Amersham), +/− compounds or 0.001 MM unlabeled glucagon. After 4-12 hours incubation at room temperature, the radioactivity bound to the cell membranes was determined in a radioactive emission detection counter (Wallac-Microbeta). Data was analyzed using the software program Prism® from GraphPad. The $IC_{50}$ values were calculated using non-linear regression analysis assuming single site competition. $IC_{50}$ values for the compounds of the invention are generally in the range of as low as about 1 nM to as high as about 500 nM, and thus have utility as glucagon antagonists.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (Top-Count-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:
1. A compound represented by formula I:

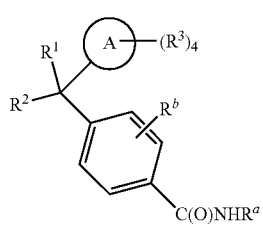

or a pharmaceutically acceptable salt thereof, wherein:
Ring A represents a bicyclic Aryl or 8-10 membered bicyclic heteroaryl group containing 1-3 heteroatoms, 0-1 of which are O or S, and 0-2 of which are N atoms;

$R^1$ is selected from $C_{1-10}$alkyl and $C_{2-10}$ alkenyl, said groups being optionally substituted with: 1-5 halo groups, up to perhalo, and 1 member selected from OH, $CO_2R^4$, $SO_pR^5$, CN, $NO_2$ $C(O)NR^6R^7$, $NR^6R^7$, $OC_{1-6}$alkyl, $C_{1-6}$haloalkoxy, halo$C_{1-6}$alkylthio, Aryl and Heteroaryl, said Aryl and Heteroaryl being optionally substituted with 1-3 halo groups and 1-2 members selected from the group consisting of: OH, $CO_2R^4$, $SO_pR^5$, CN, $NO_2$, $C(O)NR^6R^7$, $NR^6R^7$; $C_{1-6}$alkyl, halo$C_{1-6}$alkyl, $C(O)C_{1-6}$alkyl, $C(O)$-halo$C_{1-6}$alkyl, $OC_{1-6}$alkyl, halo$C_{1-6}$alkoxy $C_{2-6}$alkenyl, halo$C_{2-6}$alkenyl , $SC_{1-6}$alkyl and halo$SC_{1-6}$alkyl;

$R^2$ represents hydrogen, $C_{1-6}$alkyl or halo$C_{1-6}$alkyl;

four $R^3$ groups are present as follows:
1) 0-1 $R^3$ group is selected from the group consisting of: Aryl, HAR, —$C_{1-4}$Alkyl-Aryl, —$C_{1-4}$Alkyl-HAR, —X-Aryl, —X-HAR, —X—$C_{1-4}$Alkyl-Aryl and —X—$C_{1-4}$Alkyl-HAR; wherein X represents O, S, S(O) or S(O)$_2$;

said Aryl and HAR groups and portions of the groups above being optionally substituted with 1-4 halo atoms, and 1-2 members selected from: OH, CN, $C_{1-6}$alkyl, $OC_{1-6}$alkyl, halo$C_{1-6}$alkyl, $OC_{1-6}$haloalkyl, $NO_2$, $SO_pR^5$, $C_{2-6}$alkenyl, $OC_{2-6}$alkenyl and $NR^6R^7$;

2) 0-3 $R^3$ groups are selected from: OH, CN, oxo, $NO_2$, $SO_pR^5$, $NR^6R^7$, $C_{1-8}$alkyl, halo$C_{1-8}$alkyl, $OC_{1-8}$alkyl, $OC_{1-8}$haloalkyl, $C_{2-8}$alkenyl, $OC_{2-8}$alkenyl and halo$C_{2-8}$alkenyl, and 3) any remaining $R^3$ groups are H or halo atoms;

$R^4$ is H or $C_{1-6}$alkyl, and $R^5$ represents a member selected from the group consisting of: $C_{1-8}$alkyl, halo$C_{1-6}$alkyl, Aryl or Ar—$C_{1-4}$alkyl;

$R^6$ and $R^7$ each independently represent H or $C_{1-6}$alkyl;

p is 0, 1 or 2;

$R^a$ represents $CH_2CH_2CO_2R^4$, $CH_2CH(OH)CO_2R^4$ or 5-tetrazolyl; and $R^b$ is H or is selected from the group consisting of: halo, CN, $NO_2$, OH, $C_{1-3}$alkyl, $OC_{1-3}$alkyl, halo$C_{1-3}$alkyl and halo$C_{1-3}$alkoxy.

2. A compound in accordance with claim 1, or a pharmaceutically acceptable salt thereof, wherein ring A is selected from the group consisting of naphthyl and bicyclic 9-10 membered heteroaryl containing 1-3 heteroatoms, 0-1 of which is an oxygen or sulfur atom and 0-2 of which are nitrogen atoms.

3. A compound in accordance with claim 2, or a pharmaceutically acceptable salt thereof, wherein ring A is selected from the group consisting of naphthyl, quinolinyl, benzimidazolyl, benzothiazolyl, benzofuranyl and benzoxazolyl.

4. A compound in accordance with claim 1, or a pharmaceutically acceptable salt thereof, wherein $R^1$ represents a $C_{1-8}$alkyl group or a $C_{2-8}$alkenyl group, said groups being optionally substituted with 1-3 halo atoms, and further optionally substituted with 1 group selected from: OH, $SO_pR^5$, $OC_{1-3}$alkyl, halo$C_{1-3}$alkoxy, Aryl and HAR, said Aryl and HAR being optionally substituted with 1-3 halo atoms, and 1-2 groups selected from $SO_pR^5$, $C_{1-6}$alkyl, halo$C_{1-6}$alkyl, $OC_{1-6}$alkyl and halo$C_{1-6}$alkoxy.

5. A compound in accordance with claim 4, or a pharmaceutically acceptable salt thereof, wherein $R^1$ represents a $C_{1-8}$alkyl or a $C_{2-8}$alkenyl group, said groups being optionally substituted with 1-3 halo atoms, and further optionally substituted with 1 group selected from $SO_pR^5$ Aryl and HAR, wherein p represents 0, $R^5$ represents $C_{1-4}$alkyl, and said Aryl and HAR being optionally substituted with 1-3 halo atoms, and 1 group selected from $SO_pR^5$, $C_{1-6}$alkyl, halo$C_{1-6}$alkyl, $OC_{1-6}$alkyl and halo$C_{1-6}$alkoxy.

6. A compound in accordance with claim 1, or a pharmaceutically acceptable salt thereof, wherein $R^2$ is selected from the group consisting of:

H, $C_{1-4}$alkyl and halo$C_{1-4}$alkyl.

7. A compound in accordance with claim 1, or a pharmaceutically acceptable salt thereof, wherein four $R^3$ groups are present as follows:
1) 0-1 $R^3$ group is selected from the group consisting of: Aryl, HAR, —$C_{1-4}$Alkyl-Aryl, —X—$(CH_2)_{1-4}$Aryl, —$C_{1-4}$Alkyl-HAR and —X—$(CH_2)_{1-4}$HAR;

wherein X represents O or S and said Aryl and HAR groups and portions of the groups above being optionally substituted with 1-3 halo atoms, and 1-2 members selected from: $C_{1-6}$alkyl, $OC_{1-6}$alkyl, halo$C_{1-6}$alkyl, $OC_{1-6}$haloalkyl, $SO_pR^5$, $C_{2-6}$alkenyl, $OC_{2-6}$alkenyl, and CN;

2) 0-3 $R^3$ groups selected from: CN, $NO_2$, $SO_pR^5$, $C_{1-8}$alkyl, halo$C_{1-8}$alkyl, $OC_{1-8}$alkyl, $OC_{1-8}$haloalkyl and $C_{2-8}$alkenyl , and 3) any remaining $R^3$ groups are H or halo atoms.

8. A compound in accordance with claim 7, or a pharmaceutically acceptable salt thereof, wherein four $R^3$ groups are present as follows:
1) 0-1 $R^3$ group is selected from the group consisting of: Phenyl, a 5-6 membered HAR group, —$(CH_2)_{1-2}$-Phenyl, —X—$(CH_2)_{1-2}$-Phenyl, —$(CH_2)_{1-2}$-5-6 membered HAR and —X—$(CH_2)_{1-2}$-5-6 membered HAR, wherein X represents O or S and said Aryl and HAR groups and portions of the groups above are optionally substituted with 1-3 halo atoms, and 1 member selected from: $C_{1-6}$alkyl, $OC_{1-6}$alkyl, halo$C_{1-6}$alkyl, $OC_{1-6}$haloalkyl, $SO_pR^5$, $C_{2-6}$alkenyl, $OC_{2-6}$alkenyl, and CN;

2) 0-3 $R^3$ groups are selected from: CN, $NO_2$, $SO_pR^5$, $C_{1-8}$alkyl, halo$C_{1-8}$alkyl, $OC_{1-8}$alkyl, $OC_{1-8}$haloalkyl and $C_{2-8}$alkenyl, wherein p represents 0 and $R^5$ represents $C_{1-6}$alkyl or halo$C_{1-6}$alkyl, and 3) any remaining $R^3$ groups are H or halo atoms selected from Cl and F.

9. A compound in accordance with claim 1, or a pharmaceutically acceptable salt thereof, wherein $R^a$ is selected from

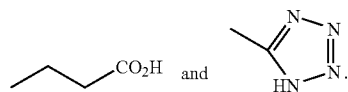

10. A compound in accordance with claim 9, or a pharmaceutically acceptable salt thereof, wherein $R^a$ represents

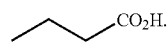

11. A compound in accordance with claim 1, or a pharmaceutically acceptable salt thereof, wherein: $R^b$ represents H.

12. A compound in accordance with claim 1, or a pharmaceutically acceptable salt thereof, wherein:

ring A is selected from the group consisting of naphthyl and bicyclic 9-10 membered heteroaryl containing 1-3 heteroatoms, 0-1 of which is an oxygen or sulfur atom and 0-2 of which are nitrogen atoms;

R[1] represents a $C_{1-8}$alkyl group or a $C_{2-8}$alkenyl group, said groups being optionally substituted with 1-3 halo atoms and further optionally substituted with 1 group selected from: OH, $SO_pR^5$, $OC_{1-3}$alkyl, halo$C_{1-3}$alkoxy, Aryl and HAR, said Aryl and HAR being optionally substituted with 1-3 halo atoms, and 1 group selected from $SO_pR^5$, $C_{1-6}$alkyl, halo$C_{1-6}$alkyl, $OC_{1-6}$alkyl and halo$C_{1-6}$alkyl;

$R^2$ is selected from the group consisting of: H, $C_{1-4}$alkyl and halo$C_{1-4}$alkyl;

four $R^3$ groups are present as follows:
  1) 0-1 $R^3$ group is selected from the group consisting of: Aryl, HAR, —$C_{1-4}$Alkyl-Aryl, —X—$(CH_2)_{1-4}$Aryl and —$C_{1-4}$Alkyl-HAR;
     wherein X represents O or S and said Aryl and HAR groups and portions of the groups above being optionally substituted with 1-3 halo atoms, and 1-2 members selected from: $C_{1-6}$alkyl, $OC_{1-6}$alkyl, halo$C_{1-6}$alkyl, $OC_{1-6}$haloalkyl, $SO_pR^5$, $C_{2-6}$alkenyl, $OC_{2-6}$alkenyl, and CN;
  2) 0-3 $R^3$ groups selected from: CN, $NO_2$, $SO_pR^5$, $C_{1-8}$alkyl, $OC_{1-8}$alkyl, $OC_{1-8}$haloalkyl and $C_{2-8}$alkenyl, and
  3) any remaining $R^3$ groups are H or halo atoms;

$R^a$ is selected from

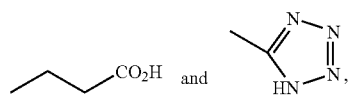

and $R^b$ represents H.

13. A compound in accordance with claim 1 selected from the following tables:

EXAMPLE 1

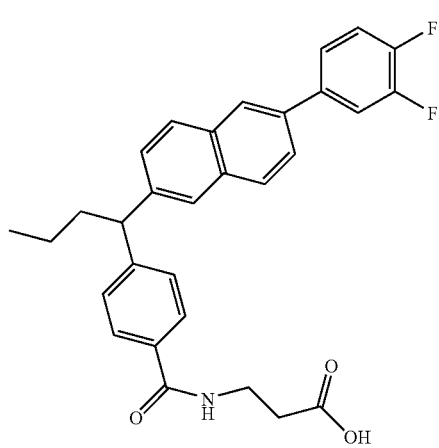

EXAMPLE 2

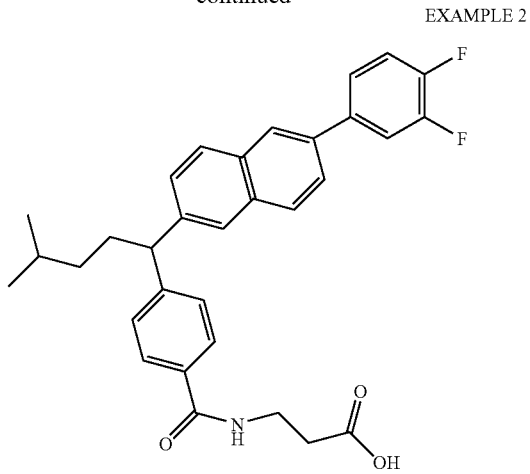

EXAMPLE 3

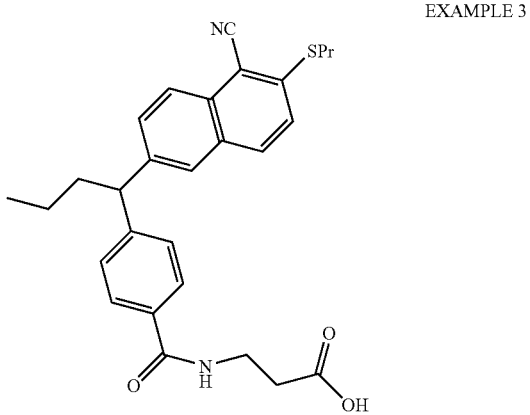

EXAMPLE 4

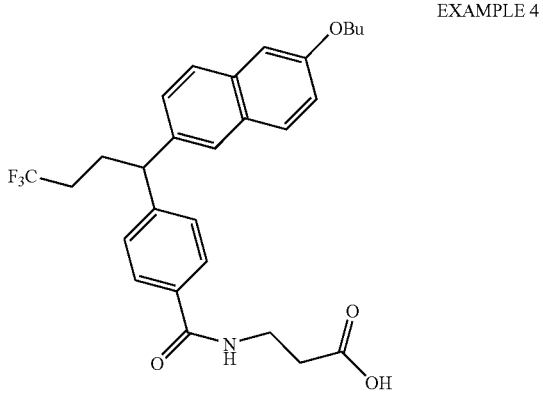

EXAMPLE 5

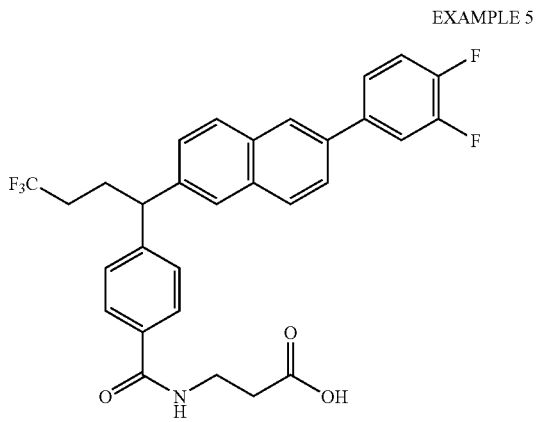

EXAMPLE 6
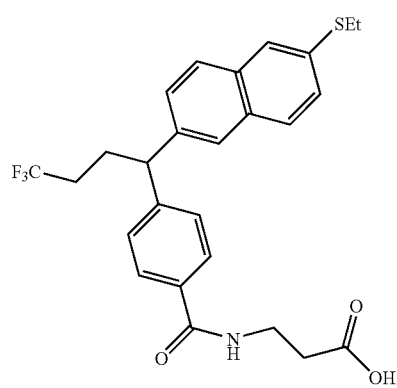
EXAMPLE 7
EXAMPLE 8
EXAMPLE 9
EXAMPLE 10
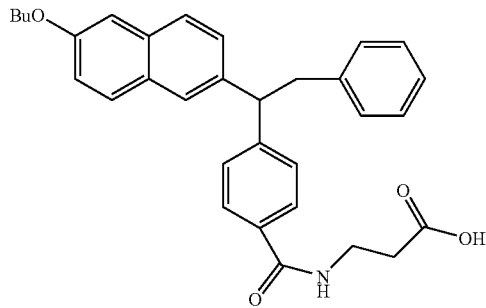
EXAMPLE 11
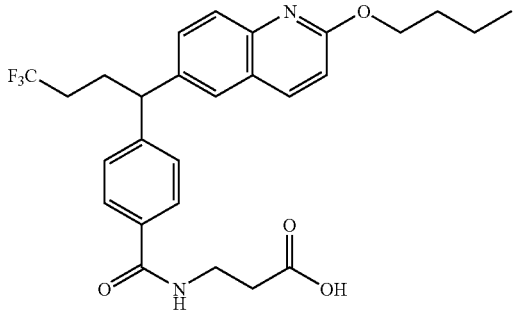
EXAMPLE 12
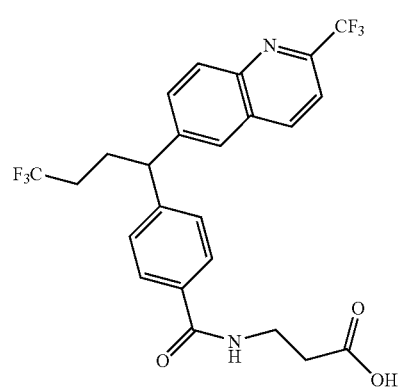
EXAMPLE 13
EXAMPLE 14
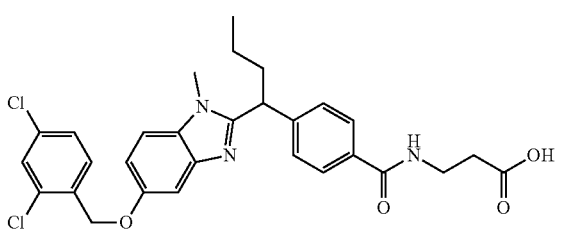

75
-continued
EXAMPLE 15
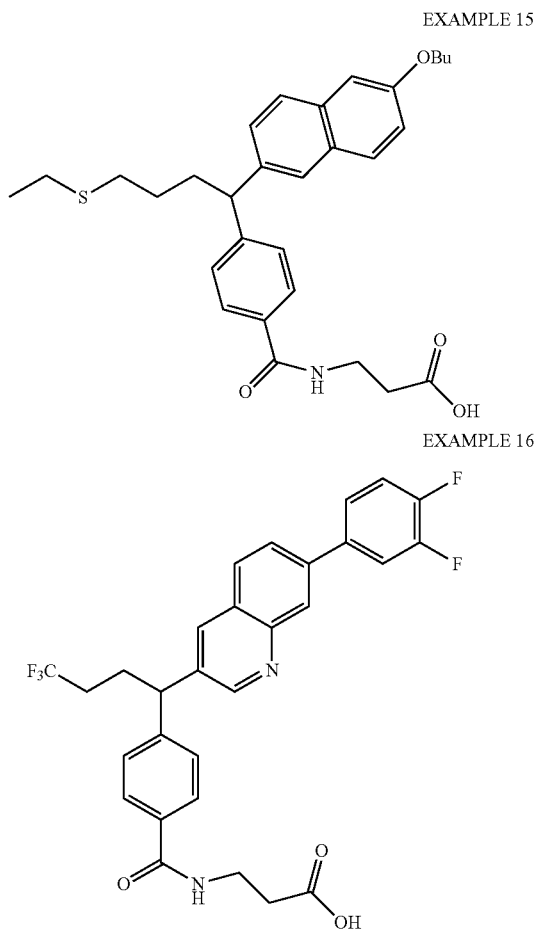
EXAMPLE 16
76
TABLE 1-continued
| Example | R³ᵃ | R³ᵇ | R³ᶜ |
|---|---|---|---|
| 20 | 3,4-dichlorophenyl | H | H |
| 21 | -pentyl | H | H |
| 22 | 3-fluorophenyl | H | H |
| 23 | 3-chloro-4-fluorophenyl | H | H |
| 24 | 3-(OCF₃)phenyl | H | H |
| 25 | 3-chloro-4-(CF₃)phenyl | H | H |
| 26 | 3,5-difluorophenyl | H | H |
| 27 | 4-chloro-3-(CF₃)phenyl | H | H |
TABLE 1
| Example | R³ᵃ | R³ᵇ | R³ᶜ |
|---|---|---|---|
| 17 | —OMe | H | H |
| 18 | —OCH₂(cyclohexyl) | H | H |
| 19 | —OCH₂(3-fluorophenyl) | H | H |

TABLE 1-continued

| Example | R³ᵃ | R³ᵇ | R³ᶜ |
|---|---|---|---|
| 28 | 3-chlorophenyl | H | H |
| 29 | thiophen-3-yl | H | H |
| 30 | 4-fluoro-3-methylphenyl | H | H |
| 31 | 4-isopropylphenyl | H | H |
| 32 | 3,5-dichlorophenyl | H | H |
| 33 | -hexyl | H | H |
| 34 | -heptyl | H | H |
| 35 | furan-3-yl | H | H |
| 36 | 2-cyclohexylethyl | H | H |
| 37 | cyclopentyl | H | H |
| 38 | 3,3-dimethylbutyl | H | H |
| 39 | 3,3-dimethylbut-1-en-1-yl | H | H |
| 40 | -Propyl | Cl | Cl |
| 41 | -Pentyl | Cl | Cl |
| 42 | cyclopent-1-en-1-yl | Cl | Cl |
| 43 | —SO₂Et | H | H |
| 44 | 4-ethoxy-2-(trifluoromethyl)phenyl (attached at position shown) — 2-substituted with CF₃, 5-position EtO | H | H |
| 45 | —OBu | CN | Cl |
| 46 | —OCF₂H | CN | Cl |
| 47 | —OPr | CN | Cl |
| 48 | —OCH₂-cyclohexyl | CN | Cl |
| 49 | —SEt | CN | Cl |
| 50 | —SEt | —SEt | Cl |

TABLE 2
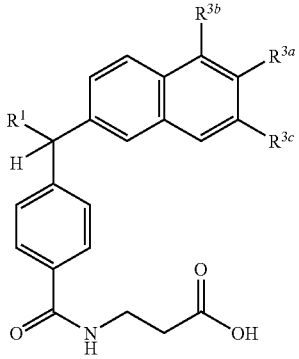
| Example[ii] | R[1] | R[3a] | R[3b] | R[3c] |
|---|---|---|---|---|
| 51[iii] | -allyl | —OButyl | H | H |
| 52 | -allyl | —OButyl | H | H |
| 53 | -hexyl | 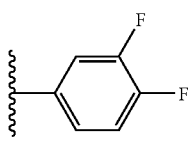 | H | H |
| 54 | 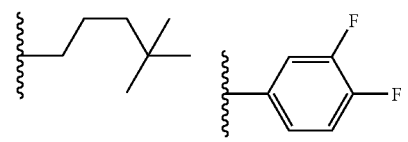 | 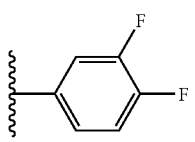 | H | H |
| 55 | -pentyl | 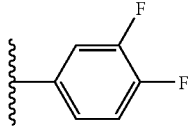 | H | H |
| 56 | -Butyl | 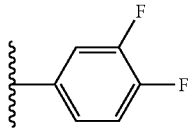 | H | H |
| 57[iv] | —Bn | —OMe | H | H |
| 58 | -Propyl | 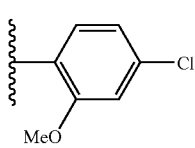 | H | H |
| 59 | -Propyl | 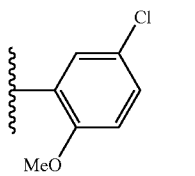 | H | H |
| 60 | -Propyl | 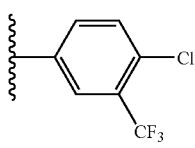 | H | H |

TABLE 2-continued
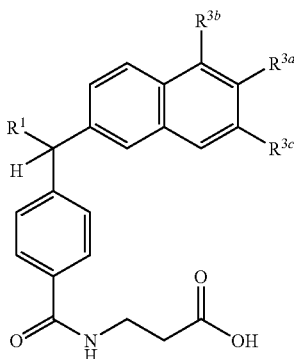
| Example[ii] | R[1] | R[3a] | R[3b] | R[3c] |
|---|---|---|---|---|
| 61 | -Propyl | 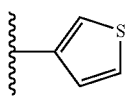 | H | H |
| 62 | -Propyl | 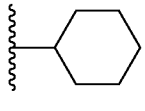 | H | H |
| 63 | -Propyl | 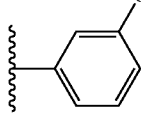 | H | H |
| 64 | -Propyl | —SEt | H | H |
| 65 | -Propyl | 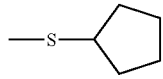 | H | H |
| 66 | -Propyl | 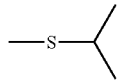 | H | H |
| 67 | -Propyl | 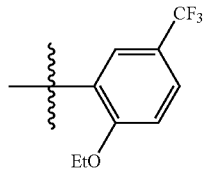 | H | H |
| 68 | -Propyl | 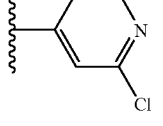 | H | H |
| 69 | -Propyl | 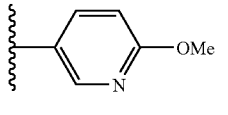 | H | H |
| 70 | -Propyl | 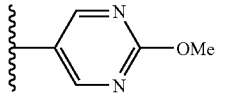 | H | H |
| 71 | -Propyl | —SPr | —CF$_3$ | H |
| 72 | -Propyl | —OBu | Cl | Cl |
| 73 | -Propyl | —OBu | —SEt | H |

TABLE 2-continued
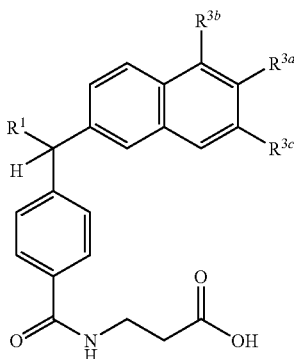
| Example[ii] | R[1] | R[3a] | R[3b] | R[3c] |
|---|---|---|---|---|
| 74 | -Propyl | —OBu | —Pr | H |
| 75 | -Propyl | 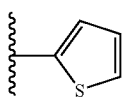 | H | H |
| 76 | -Propyl | 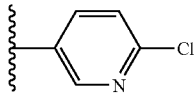 | H | H |
| 77 | -Propyl | 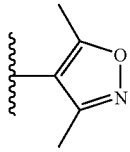 | H | H |
TABLE 3
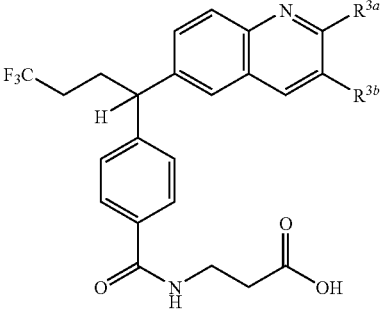
| Example | R[3a] | R[3b] |
|---|---|---|
| 78 | 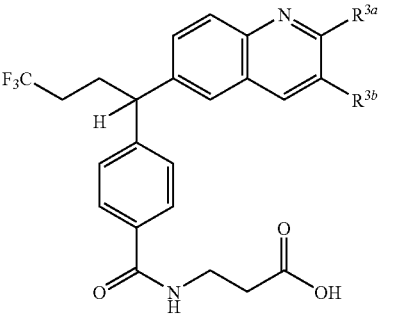 | H |
| 79 | -hexyl | H |
| 80 | 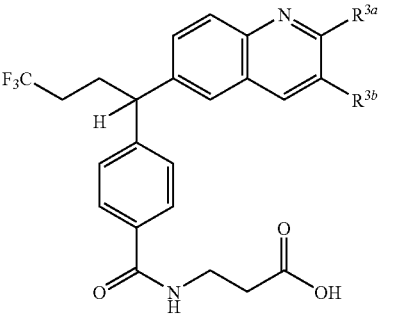 (3,4-F) | Cl |
| 81 | —OBu | Cl |
| 82 | —SEt | H |
| 83 | —SCF$_2$H | H |

TABLE 4
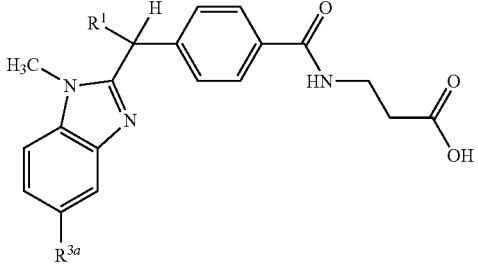
| Example | R¹ | R³ᵃ |
|---|---|---|
| 84 | 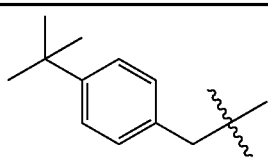 | Br |
| 85 |  | OMe |
| 86 | n-hexyl | 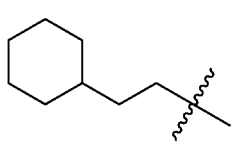 |
| 87 | n-hexyl |  |
| 88 | 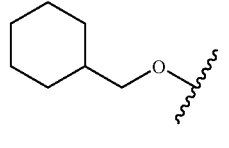 |  |
| 89 | 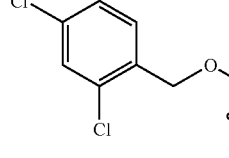 | 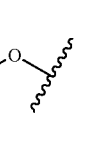 |
| 90 | 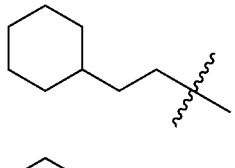 | 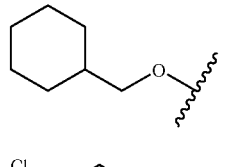 |
or a salt thereof.
14. A pharmaceutical composition comprising a compound in accordance with claim 1, or a pharmaceutically acceptable salt thereof, in combination with a pharmaceutically acceptable carrier.
* * * * *